US006627177B2

(12) United States Patent
Singaram et al.

(10) Patent No.: US 6,627,177 B2
(45) Date of Patent: *Sep. 30, 2003

(54) POLYHYDROXYL-SUBSTITUTED ORGANIC MOLECULE SENSING OPTICAL IN VIVO METHOD UTILIZING A BORONIC ACID ADDUCT AND THE DEVICE THEREOF

(75) Inventors: Bakthan Singaram, Santa Cruz, CA (US); Ritchie A. Wessling, Watsonville, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/731,323

(22) Filed: Dec. 5, 2000

(65) Prior Publication Data

US 2002/0106326 A1 Aug. 8, 2002

(51) Int. Cl.⁷ .......................... A61B 10/00; A61B 5/00; A61B 8/00; A01N 33/02; A61K 31/135
(52) U.S. Cl. .................... 424/9.6; 514/646; 514/741; 514/765
(58) Field of Search .................. 424/9.6; 514/646, 514/741, 765

(56) References Cited

U.S. PATENT DOCUMENTS

| | | | |
|---|---|---|---|
| 4,659,817 A | 4/1987 | Gallop et al. | 540/541 |
| 4,886,338 A | 12/1989 | Yafuso et al. | 350/96.29 |
| 5,039,491 A | 8/1991 | Sasaki et al. | 422/82.05 |
| 5,114,676 A | 5/1992 | Leiner et al. | 422/82.06 |
| 5,137,833 A * | 8/1992 | Russell | 436/94 |
| 5,232,858 A | 8/1993 | Wolfbeis et al. | 43/77 |
| 5,242,842 A | 9/1993 | Sundrehagen | 436/536 |
| 5,244,562 A | 9/1993 | Russell | 204/418 |
| 5,466,798 A | 11/1995 | Singaram et al. | 540/541 |
| 5,503,770 A * | 4/1996 | James et al. | 252/301.16 |
| 5,512,246 A | 4/1996 | Russell et al. | 422/57 |
| 5,517,313 A | 5/1996 | Colvin, Jr. et al. | 356/417 |
| 5,631,364 A | 5/1997 | Sundrehagen et al. | 540/128 |
| 5,739,318 A * | 4/1998 | Frantzen et al. | 540/128 |
| 5,763,238 A | 6/1998 | James et al. | 436/172 |
| 5,777,060 A | 7/1998 | Van Antwerp et al. | 528/28 |
| 5,786,439 A | 7/1998 | Van Antwerp et al. | 528/77 |
| 5,852,126 A | 12/1998 | Barnard et al. | 525/326.3 |
| 5,882,494 A | 3/1999 | Van Antwerp | 204/403 |
| 5,894,351 A | 4/1999 | Colvin, Jr. et al. | 356/417 |
| 5,922,612 A | 7/1999 | Alder et al. | 436/163 |
| 6,002,954 A * | 12/1999 | Van Antwerp et al. | 600/317 |
| 6,011,984 A * | 1/2000 | Van Antwerp et al. | 600/317 |
| 6,063,637 A | 5/2000 | Arnold et al. | 436/94 |
| 6,304,766 B1 | 10/2001 | Colvin, Jr. | 600/317 |
| 6,319,540 B1 | 11/2001 | Van Antwerp et al. | 427/2.13 |
| 6,330,464 B1 | 12/2001 | Colvin, Jr. et al. | 600/316 |
| 6,366,793 B1 | 4/2002 | Bell et al. | 600/317 |
| 6,387,672 B1 | 5/2002 | Arimori et al. | 435/183 |
| 6,485,703 B1 | 11/2002 | Cote et al. | 424/9.1 |
| 2001/0034479 A1 * | 10/2001 | Ring et al. | 600/322 |

FOREIGN PATENT DOCUMENTS

| | | | | |
|---|---|---|---|---|
| WO | WO 92/08722 | 5/1992 | | C07F/5/02 |
| WO | WO 97/19188 | 5/1997 | | C12Q/1/100 |
| WO | WO 01/74968 A2 | 10/2001 | | C09K/11/00 |

OTHER PUBLICATIONS

H. Suenaga, S. Arimori and S. Shinkai, Sugar–Controlled Association–Dissociation Equilibria Between DNA and Boronic Acid–Appended Porphyrin, J. Chem. Soc., Perkin Trans. 2, 1996, pp. 607–612.

Zhujun et al., A Fluorescence Sensor For Quantifying pH in the Range From 1.5 to 8.5, Anal Chim. ACTA, 1984, vol. 160, pp. 47–55.

F. C. Lightstone et al., Theoretical Study of The Boron–Nitrogen Dative Bond In Aminomethylphenyl Boronates, American Chemical Society 219th National Meeting, San Francisco, CA, Mar. 26–30, 2000, Abstract COMP 115.

D. R. Cary et al., Boronic Acid Derivatives Of Rhenum And Rethenium For The Recognition of Saccharides, American Chemical Society 219th National Meeting, San Francisco, CA, Mar. 26–30, 2000, Abstract INOR 422.

D. R. Cary et al., New Small–Molecule Glucose Transducers Based on Naphthalimide Dyes, American Chemical Society 220th National Meeting, Washington, DC, Aug. 20–24, 2000, Abstract ORGN 43.

J. A. Tran, Synthesis of a Benzophenoxazinone Boronate as a Novel Fluorescent Glucose Sensor, American Chemical Society 220th National Meeting, Washington, DC, Aug. 20–24, 2000, Abstract ORGN 237.

P.D. Hale, et al., Investigation of Viologen Derivatives Electron–Transfer Mediators in Amperometric Glucose Sensors, Analytica Chimica Acta, vol. 248: 155–161, (1991).

D. E. Smith, et al., Entropy of Association of Methane in Water: A New Molecular Dynamics Computer Simulation, J. Am. Chem. Soc., 114:5875–5876 (1992).

A. B. Kotlyar, et al., The Dynamics of Proton Transfer at the C Side of the Mitochondrial Membrane: Picosecond and Micosecond Measurements, Biochemistry, 33:873–879 (1994).

E.T.B. Al–Takrity, Synthesis of Poly(Methacrylic Acid) Bearing Fluorescent and Fluorescence–Quenching Groups, Euro. Polym. J., 31(4):383–385 (1995).

(List continued on next page.)

*Primary Examiner*—Sreeni Padmanabhan
*Assistant Examiner*—Lauren Q. Wells
(74) *Attorney, Agent, or Firm*—Peters, Verny, Jones & Schmitt, L.L.P.; Howard M. Peters

(57) ABSTRACT

The present invention concerns an improved optical method and optical sensing device for determining the levels of polyhydroxyl-substituted organic molecules in vivo in aqueous media. Specifically, a dye is combined with a conjugated nitrogen-containing heterocyclic aromatic boronic acid-substituted bis-onium compound in the presence of a sugar, such as fructose or glucose. The viologens are preferred as the aromatic conjugated nitrogen-containing boronic acid substituted compounds. The method is useful to determine sugar levels in a human being.

17 Claims, 8 Drawing Sheets

OTHER PUBLICATIONS

H. Murakami, et al., Sugar Sensing Utilizing Aggregation Properties of Boronic–Acid–Appended Porphyrins and Metalloporphyrins, J. Chem. Soc. Perkin Trans 2:975–981 (1994).

H. Shinmori, et al., Spectroscopic Sugar Sensing by a Stilbene Derivative with Push (Me2N)–Pull((HO)2B–)–Type Substituents, Tetrahedron, 51(7):1893–1902 (1995).

H. Murakami, et al., Sugar Sensing Utilizing Aggregation Properties of Boronic–Acid–Appended Porphyrin, Tetrahedron Letters, 34(39):6273–6276 (1993).

T. D. James, et al., A Glucose–Selective Molecular Fluorescence Sensor, Angew. Chem. Int. Ed. Engl. 33(21):2207–2209 (1994).

Shinkai, et al., by Trans–3,3–Stilbenediboronic Acid: Rigidification of the Stilbene Skeleton Upon Formation of a . . . , J. Chem Soc., Chem. Commun., 1621–1622 (1994).

G. Deng, et al., Allosteric Interaction of Metal Ions with Saccharides in a Crowned Diboronic Acid, J. Am. Chem. Soc., 116:4567–4572 (1994).

K.R.A. Sandanayake, et al., Novel Molecular Sensors for Saccharides Based on the Interaction of Boronic Acid and Amines: Saccharide Sensing in Neutral Water, J. Chem. Soc., Chem. Commun., 1083–1084 (1994).

T. D. James, et al., Novel Photoinduced Electron–Transfer Sensor for Saccharides Based on the Interaction of Boronic Acid and Amine, J. Chem. Soc., Chem. Commun., 477–478 (1994).

K.R.A. Samankumara Sandanayake, et al., Molecular Fluorescence Sensor for Saccharides Based on Amino Coumarin, Chemistry Letters, 139–140 (1995).

Masayuki Takeuchi, et al., Fluorescence and CD Spectroscopic Sugar Sensing a Cyanine–appended Diboronic Acid Probe, Tetrahedron, 52(4):1195–1204 (1996).

Hibaru Suenaga, et al., Screening of Boronic Acids for Strong Inhibition of the Hydrolytic Activity of alpha–chymotrypsin and for Sugar Sensing Associated with a Large Fluorescence Change, Pure & Appl. Chem., 68(11):2179–2186 (1996).

Stephen G. Schulman, et al., Dependent of the Fluorescence of Immobilized 1–hydroxypyrene–3,6,8–Trisulfonate on Solution pH: Extension of the Range of Applicability of a pH Fluoresensor, Analytica Chimica Acta, 304, 165–170 (1995).

Hibaru Suenaga, et al., Screening of Fluorescent Boronic Acids for Sugar Sensing Which Show a Large Fluorescence Change, Tetrahedron Letters, 36(27):4825–4828 (1995).

Tony D. James, et al., Novel Fluorescence Sensor for Small Saccharides, Chem. Commun., 71–72 (1997).

Fabbrizzi, et al, Fluorescent Sensor of Imidazole and Histidine, Chem. Commun., 581–582 (1997).

K.R.A. Samankumara Sandanayake, et al., Two Dimensional Photoinduced Electron Transfer (PET) Fluorescence Sensor, Chemistry Letters, 503–504 (1995).

Jens Chr. Norrild, et al., Evidence for Mono–and Bisdentate Boronate Complexes of Glucose in the Furanose Form. Application of $^1Jc$–c Coupling Constants as a Structural Probe, J. Am. Chem. Soc., 117:1479–1484 (1995).

Fumio Ohseto, et al., Allosteric Communication between the Metal–binding Lower Rim and the Sugar–binding Upper Rim on a Calix[4]crown Platform, Tetrahedron Letters, 36(38):6911–6914 (1995).

Kazunori Kataoka, et al., Novel Sensing System for Glucose Based on the Complex Formation Between Phenylborate and Fluorescent Diol Compounds, J. Biochem., 117:1145–1147 (1995).

Tony D. James, et al., Novel Saccharide–Photoinduced Electron Transfer Sensors Based on the Interaction of Boronic Acid and Amine, J. Am. Chem. Soc., 117:8982–8987 (1995).

Patrick Linnane, et al., The Synthesis and Properties of a Calixarene–based Sugar Bowl, J. Chem. Soc., Chem. Commun., 1997–1998 (1995).

Susumu Arimori, et al., Sugar–Sensing by Chiral Orientation of Dimeric Boronic–Acid–Appended Porphyrins Which Show Selectivity for Glucose and Xylose, Chemistry Letters, 77–78 (1996).

Kazuaki Nakashima, et al., Diaza–18–crown–6–based Sugar Receptor Bearing Two Boronic Acids. Possible Communication Between Bound Sugars and Metal Cations, Chemistry Letters, 443–444 (1995).

Alexander B. Kotlyar, et al., Fast Redox Perturbation of Aqueous Solution by Photoexcitation of Pyranine, Photochemistry and Photobiology, 63(4):448–454 (1996).

Masayuki Takeuchi, et al., Chiral Sugar Recognition by a Diboronic–Acid–Appended Binaphthyl Derivative Through Rigidification Effect, Tetrahedron, 53(25):8335–8348 (1997).

Aiichiro Ori et al., Electrochemical Detection of Saccharides by the Redox Cycle of a Chiral Ferrocenylboronic Acid Derivative: A Novel Method for Sugar Sensing, Chem., Soc., Chem. Commun., 1771–1774 (1995).

Masayuki Takeuchi, et al., A Novel Sugar Sensing System Designed with a Cooperative Action of a Boronic–Acid–Appended Zinc Porphyrin and a 3–Pyridylboronic Acid Axial Ligand, Bull. Chem. Soc., Jpn., 70:699–705 (1997).

Hideyuki Shinmori, et al., Spectroscopic Detection of Diols and Sugars by a Coulour Change in Boronic Acid–Appended Spirobenzopyrans, J. Chem. Soc., Perkins Trans. 2, 1–3 (1996).

Kenichi Nakashima, et al., Fluorescence Quenching of 1–Pyrenemethanol by Methylviologen in Polystyrene Latex Dispersions, Photochemistry and Photobiology, 64(2):296–302 (1996).

Rolf Uggla, et al., Boronic Acids as Molecular Sensors NBO Analysis and 13C Chemical Shifts as Tools for Evaluation of DFT Geometry Optimization of Complexes of Diphenylmethane 3,3'–Diboronic Acids and Glucose, Tetrahedron Asymmetry, 7(6):1741–1748 (1996).

Seiji Shinkai, et al., Molecular Design of Artificial Sugar Sensing Systems, Trends in Analytical Chemistry, 15(5):188–194 (1996).

U.E. Spichiger, Biomimetic Recognition Elements for Sensor Applications, Frontiers in Biosciences: Fundamental Aspects, 27–48 (1997).

Mauricio S. Matos, et al., Spectroscopic and Kinetic Study of the Molecular Association Between Pyrene and Benzyl Viologen, Spectrochimica Acta, Part A, 54:1857–1867 (1998).

Hanne Eggert, et al., A New Glucose–Selective Fluorescent Bisboronic Acid, First Report of Strong alpha–Furanose Complexation in Aqueous Solution at Physiological pH, J. Org. Chem., 64:3846–3852 (1999).

Ryan J. Russell, et al., A Fluorescene–Bases Glucose Biosensor Using Concanavalin A and Dextran Encapsulated in a Poly(ehtylene glycol) Hydrogel, Anal., Chem., 71:3126–3132 (1999).

B. Appleton, et al., Detection of Total Sugar Concentration Using Photoinduced Electron Transfer Materials: Development of Operationally Stable, Reusable Optical Sensors, Sensors and Actuators B, 65:302–304 (2000).

George S. Wilson, et al., Enzyme–Based Biosensors for In Vivo Measurements, Chem. Rev., 100:2693–2704 (2000).

Bruce W. Bode, et al., Continuous Glucose Monitoring Used to Adjust Diabetes Therapy Improves Glycosylated Hemoglobin: A Pilot Study, Diabetes Research and Clinical Practice, 46:183–190 (1999).

Liaohai Chen, et al., Highly Sensitive Biological and Chemical Sensors Based on Reversible Fluorescence Quenching in a Conjugated Polymer, PNAS, 96(22):12287–12292, (Oct. 26, 1999).

Peter S. Heeger, et al., Making Sense of Polymer–Based Biosensors, PNAS, (96)22):12219–12221, (Oct. 26, 1999).

E. B. deBorba, et al., Photophysical and Photochemical Properties of Pyranine/Methyl Viologen complexes in Solution and in Supramolecular Aggregates: A Switchable Complex, Langmuir, 16:5900–5907 (2000).

Liat Genoser, et al., Ultrafast Direct Photoacid–Base Reaction, J. Phys. Chem. A, 104:6689–6698 (2000).

Roger J. McNichols, et al., Optical Glucose Sensing in Biological Fluids: An Overview, Journal of Biomedical Optics, 5(1):5–16 (Jan. 2000).

Jian Wang, et al., Photoluminescence of Water–Soluble Conjugated Polymers: Origin of Enhanced Quenching by Charge Transfer, Macromolecules, 33:5153–5158 (2000).

Abstracts, American Chemical Society Division of Organic Chemistry $200^{th}$ ACS Meeting, Washington DC, Aug. 20–24, 2000, #43, #237, #245 and #254.

The Dangerous Toll of Diabetes, American Diabetes Association (2000).

Anthony P. F. Turner, et al., In Vitro Diagnostics in Diabetes: Meeting the Challenge, Clinical Chemistry, 45:9, 1596–1601 (1999).

* cited by examiner where n is approximately 125

FIG._3A
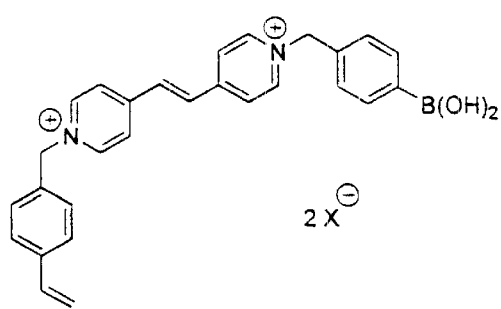
FIG._3C
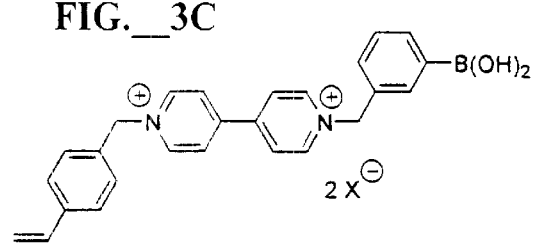
FIG._3B
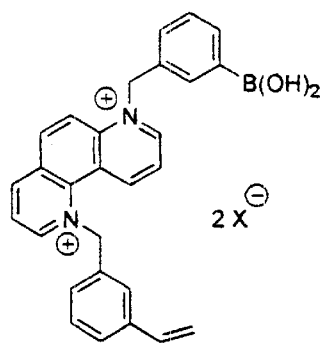
FIG._3D
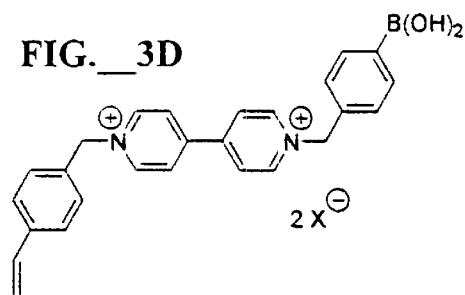

Semi-IPN

IPN

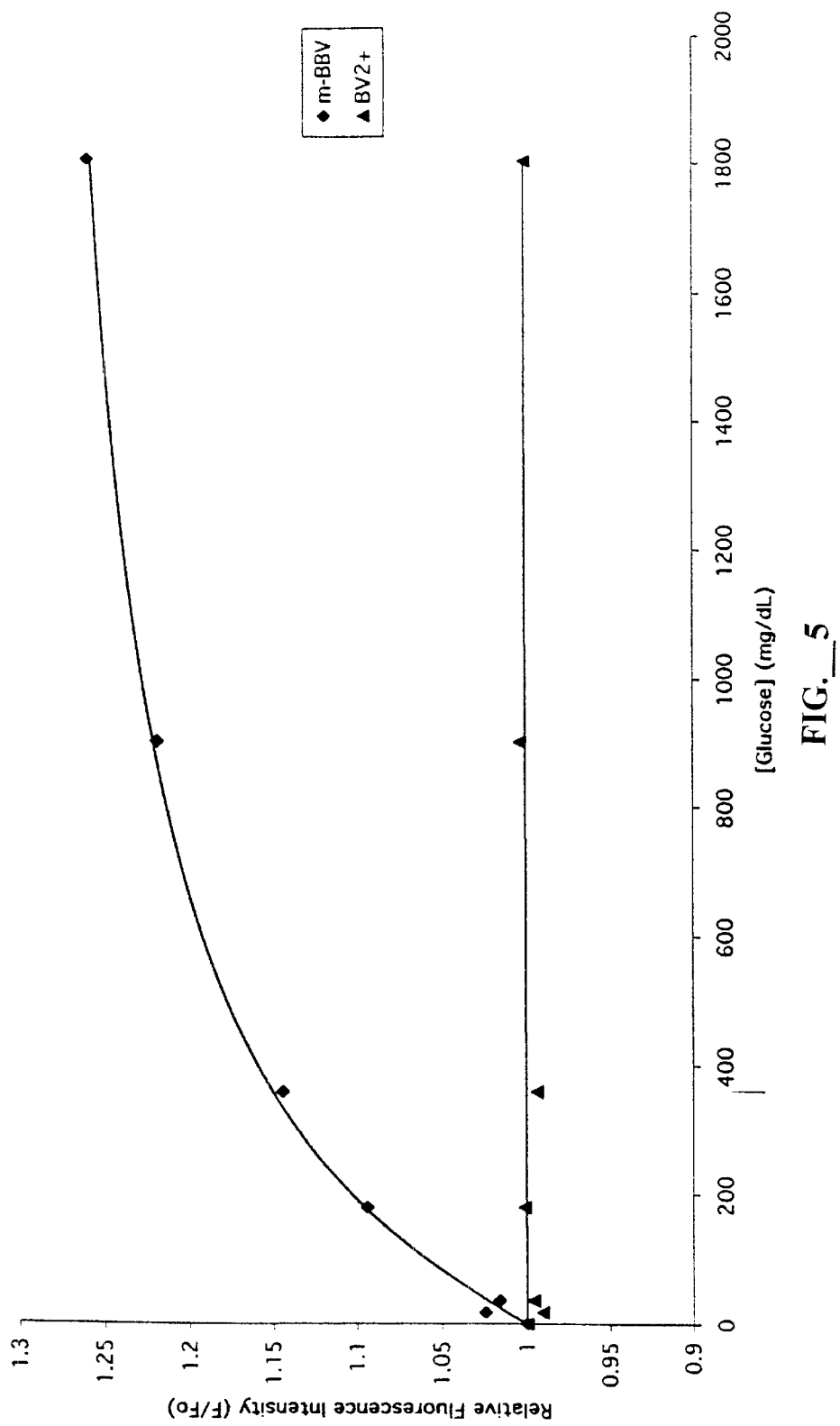

POLYHYDROXYL-SUBSTITUTED ORGANIC MOLECULE SENSING OPTICAL IN VIVO METHOD UTILIZING A BORONIC ACID ADDUCT AND THE DEVICE THEREOF

BACKGROUND OF THE INVENTION

1. Field of the Invention

This invention relates to an improved optical method and sensor for polyhydroxy substituted organic molecules that measure the concentration of these molecules in aqueous media. In particular, the method and sensor monitor the concentration of sugars, i.e. glucose or fructose, in aqueous solution in vivo. The determination of glucose in physiological fluids in vivo is of particular importance. The sensing device is implanted in a human being. Some of the novel components of the optical method and device are also considered to be inventions in their own right.

2. Description of Related Art

There has been an ongoing effort over many years to use fluorescence techniques to measure polyhydroxyl compound (e.g. glucose) concentrations in body fluids. Although the term "glucose" is used herein below, it is to be understood that the concentration of most polyhydroxyl-containing organic compounds (carbohydrates, 1,2-diols, 1,3-diols and the like) in a solution are determined. But in spite of the intense effort, no practical system has been developed and commercialized for in vivo monitoring. Several attempts have been made to detect glucose by fluorescence using dyes to which a boronic acid group has been attached. Boronic acids are known to bind sugars reversibly. When the boronic acid functional dye binds to a sugar, the properties of the dye are affected. These changes have been used in the past to measure sugar concentration.

One use of this approach to a glucose sensor was reported by Russell U.S. Pat. No. 5,137,833 (See also Russell & Zepp, U.S. Pat. No. 5,512,246) which disclosed the use of a boronic acid functionalized dye that binds to glucose and generate a signal dependent on glucose concentration. James et al U.S. Pat. No. 5,503,770 used the same principle but combined a fluorescent dye, an amine quenching functionality, and a boronic acid in a single complex moiety, the fluorescence emission from which varies with extent of glucose binding. Van Antwerp et al U.S. Pat. Nos. 6,002,954 and 6,011,984 combined features of the previously cited references and also taught fabrication of a device that is purported to be implantable.

Patents of interest include but are not limited to:
Russell, U.S. Pat. No. 5,137,833 (1992)
James et al, U.S. Pat. No. 5,503,770 (1996)
Russell & Zepp, U.S. Pat. No. 5,512,246 (1996)
Van Antwerp et al, U.S. Pat. No. 6,002,954 (1999)
Van Antwerp and Mastrototaro, U.S. Pat. No. 6,011,984 (2000)
Related U.S. patents of interest include:
Wolfbeis et al, U.S. Pat. No. 4,586,518 (1986)
Gallop & Paz, U.S. Pat. No. 4,659,817 (1989)
Yafuso & Hui, U.S. Pat. No. 4,798,738 (1989)
Yafuso & Hui, U.S. Pat. No. 4,886,338 (1989)
Saaski et al, U.S. Pat. No. 5,039,491 (1991)
Lanier et al, U.S. Pat. No. 5,114,676 (1992)
Wolfbeis et al, U.S. Pat. No. 5,232,858 (1993)
Colvin, U.S. Pat. No. 5,517,313 (1996)
Sundrehagen et al, U.S. Pat. No. 5,631,364 (1997)
James et al, U.S. Pat. No. 5,763,238 (1998)
Siegmund et al, U.S. Pat. No. 5,711,915 (1998)
Bamard & Rouilly, U.S. Pat. No. 5,852,126 (1998)
Colvin, U.S. Pat. No. 5,894,351 (1999)
Alder et al, U.S. Pat. No. 5,922,612 (1999)
Arnold et al, U.S. Pat. No. 6,063,637 (2000)
Song et al, U.S. Pat. No. 6,046,312 (2000)
Kimball et al, U.S. Pat. No. 6,139,799 (2000)
Clark et al., U.S. Pat. No. 6,040,194 (2000)
Related articles and publications of interest include:
Yoon & Czarnik, J. Amer. Chem. Soc. (1992) 114, 5874–5875
James, Linnane, & Shinkai, Chem.Commun. (1996), 281–288
Suenaga et al, Tetrahedron Letters (1995), 36, 4825–4828
Eggert et al, J.Org.Chem. (1999), 64, 3846–3852
Wolfbeis et al, Analytica Chimica Acta (1995), 304, 165–170
Wang et al, Organic Letters (1999), 1, 1209–1212
Chen et al, Proc. Nat. Acad. Sci. (1999), 96, 12287–12292
P. D. Hale et al, Analytica Chimica Acta (1999), 248, 155–161
A. E. Colvin, Jr. et al, Johns Hopkins Technical Digest, Vol.12, #17, p. 378 (1996)
Murakami et al, Chem. Letters (Japan) (2000), (8), p. 940–941.
References of a general nature include:
A. W. Czarnik (ed), Fluorescent Chemosensors for Ion and Molecule Recognition, ACS Washington, D.C. 1992.
F. W. Scheller et al (eds), Frontiers in Biosensorics I Fundamental Aspects, Birkhäuser Verlag, Basel 1997.
J. R. Lakowicz, Principles of Fluorescence Spectroscopy $2^{nd}$ ed. Kluwer Academics/Plenum Publishers, New York, N.Y. (1999).
Haugland, R. P. Handbook of Fluorescent Probes and Research Chemicals $6^{th}$ ed. Molecular Probes Inc. Eugene, Oreg. (1996).

All patents, articles, references, standards and the like cited in this application are incorporated herein by reference in their entirety.

All of these prior art sensors are deficient in one or more aspects, such as operability under physiological conditions, stability of operation, simplicity of design, reliability, implantability, and sensitivity. The present invention overcomes these deficiencies.

SUMMARY OF THE INVENTION

This present invention concerns an optical method and an optical device for determining in vivo the concentrations of polyhydroxyl compounds, especially sugars such as glucose or fructose, in physiological media. These compounds, the analytes, are in a system with a fluorescence sensing device comprised of a light source, a detector, and the active components including a fluorophore (fluorescent dye), a quencher and an optional polymer matrix. Some components are inventions in their own right. When excited by light of appropriate wave length, the fluorophore emits light (fluoresces). The intensity of the light is dependent on the extent of quenching. The fluorophore and quencher are preferably independent entities, optionally they are immobilized in or covalently attached to a polymeric matrix which is permeable to or in contact with the compounds of interest to be detected and quantified.

In one aspect, the present invention comprises a class of fluorescence quenching compounds that are responsive to the presence of polyhydroxyl compounds such as glucose in aqueous media at or near physiological pH. In other words, the quenching efficiency is controlled by the concentration of these compounds in the medium. The quencher is comprised of a viologen substituted with at least one boronic acid group wherein the adduct is immobilized in or covalently bonded to a polymer. The quencher, dye and polymer may also be covalently bonded to each other.

The combination of boronic acid and viologen, and the resultant effect on viologen properties are important embodiments of the present invention.

In another aspect, the present invention is a class of polymeric fluorescent dyes which are susceptible to quenching by the viologen/boronic acid adduct. Useful dyes include pyranine derivatives (e.g. hydroxypyrene trisulfonamide derivatives and the like). (See FIGS. 1 and 2), In one embodiment, the dye is comprised of a hydroxypyrene trisulfonamide moiety bonded to a polymer. Converting sulfonic acid groups to sulfonamide groups shifts the pKa of pyranine into a range more suitable for measurement at physiological pH. This conversion also shifts the absorbance of the dye to longer wavelengths thereby allowing it to be more efficiently excited by light from a blue LED which is a preferred light source for an implanted sensor. These derivatives are typically prepared by reacting a trisulfonyl chloride intermediate with 1) a polyamine, 2) an amine functional ethylenically unsaturated monomer which adduct is subsequently polymerized, 3) or an amine functional polymer. Preferably, the dye is a fully substituted trisulfonamide containing no residual sulfonic acid groups.

In another aspect, the present invention is a composite water-compatible polymer matrix, preferably a hydrogel, which comprises the dye and quencher moieties. The matrix is a water-swellable copolymer, preferably crosslinked, to which the dye and quencher moieties are covalently bonded. More preferably, the matrix is an interpenetrating polymer network (IPN) with the dye incorporated in one polymer network and the quencher in the other polymer network. Most preferably the matrix is a semi-IPN wherein the dye component is a high molecular weight water-soluble or dispersible polymer trapped in a crosslinked network comprised of quencher monomer and suitable hydrophilic comonomers. Optionally, the quencher may be in the water-compatible or dispersible component and the dye within the network. Further both dye and quencher may be separately incorporated in water-soluble or dispersible polymers wherein dye and quencher are both trapped in an inert polymer matrix. Optionally, the components are separated from the analyte solution by a membrane which is impermeable to the components, but permeable to the analyte. Optionally, the matrix is molecularly imprinted to favor association between dye and quencher, and to enhance selectivity for specific sugars, e.g. glucose, over other polyhydroxy compounds.

In another aspect, the present invention concerns a device for measuring the concentration of glucose in vivo by means of an optical sensor. The specific device is comprised of a visible light source, preferably a blue LED light source, a photodetector, a light conduit such as an optical fiber assembly, and a water-insoluble polymer matrix comprised of a fluorophore susceptible to quenching by a viologen, a viologen/boronic acid quencher, and a glucose permeable polymer, wherein the matrix is in contact with said conduit and with the medium containing the analyte.

In another embodiment the present invention relates to an optical method for the in vivo detection between about 430 and 800 nm of polyhydroxyl-substituted organic molecules as the analyte in a physiological fluid, at pH of about 7.3 to 7.5, which method comprises:

A. obtaining a fluorophore dye D, which is compatible with the analyte solution, wherein D is selected from:
  a) $D^1$ which is a fluorophore dye having the properties of:
    i. A fluorophore,
    ii. An excitation in the range greater than 430 nm and less than 800 nm,
    iii. Resistant to photobleaching under the conditions of analysis,
    iv. A Stokes shift of about or greater than 30 nm,
    v. Compatibility with said analyte solution, and wherein
    vi. Said Dye $D^1$ is quenched by methyl viologen to produce an experimentally determined apparent Stern-Volmer quenching constant (Ksv) greater than or equal to 50,
    wherein the fluorophore dye $D^1$ is a discrete compound having a molecular weight of 1,000 daltons or greater or is a pendant group or chain unit in a water soluble or dispersible polymer having a molecular weight greater than about 10,000 daltons, optionally said polymer is non-covalently associated with a water insoluble polymer matrix $M^1$ and is physically immobilized within said polymer matrix $M^1$; and wherein said polymer matrix $M^1$ is permeable to or in contact with said analyte solution;
  (b) $D^2$ is a fluorophore dye having the properties of:
    i. A fluorophore,
    ii. An excitation in the range greater than 430 nm and less than 800 nm,
    iii. A Stokes shift of about or greater than 30 nm,
    iv. Resistant to photobleaching under the conditions of analyses,
    v. Compatibility in the analyte solution, and wherein
    vi. Said Dye $D^2$ is quenched by methyl viologen to produce an apparent Stern-Volmer quenching constant (Ksv) greater than or equal to 50, wherein $D^2$ is covalently bonded to a water-insoluble polymer matrix $M^1$ wherein said polymer matrix $M^1$ is permeable to or in contact with said analyte; wherein said fluorophore dye $D^2$ is a part of the structure:

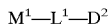

wherein:
      $M^1$ is said polymer matrix, $L^1$ is a hydrolytically stable divalent linking group selected from a direct bond and a lower alkylene having 1 to 8 carbon atoms, optionally terminated with or including one or more divalent connecting groups selected from sulfonamide, amide, ester, ether, sulfide, sulfone, phenylene, urethane, urea, thiourea or amine, and
      $D^2$ is said fluorophore dye which is covalently bonded to said polymer matrix $M^1$, with the proviso that $D^2$ which is polyfunctional is bonded to matrix $M^1$ at one, two or three sites;

B. combining with an analyte solution-compatible boronic acid-containing quencher molecule Q, wherein Q is a conjugated nitrogen-containing heterocyclic aromatic bis-onium salt selected from:
  (i) $Q^1$ which is a pendant group or a chain unit in a water-soluble or water-dispersible polymer having a molecular weight greater than 10,000 daltons and said polymer optionally is non-covalently associated with the optional polymer matrix $M^1$ when present and immobilized within said polymer matrix $M^1$, wherein $Q^1$ is a compound having the properties of: compatibility in said analyte solution,
    produces a detectable change in the emission of the dye in the presence of said analyte, or
  (ii) $Q^2$ which is a structure having the properties of: compatibility in said analyte solution
    produces a detectable chance in the emission of the dye in the presence of said analyte,
    wherein $Q^2$ is covalently bonded by a linking group $L^2$ to $M^1$ or to a second water-insoluble polymer matrix $M^2$ producing $M^2$—$L^2$—$Q^2$ wherein $L^2$ is selected from a direct bond and a lower alkylene having 1 to 8 carbon atoms, optionally terminated with or including one or more divalent connecting groups selected from sulfonamide, amide, ester, ether, sulfide, sulfone, phenylene, urethane, urea, thiourea or amine,
    wherein said quencher $Q^1$ or $Q^2$ is mixed at a molecular level with said fluorophore dye $D^1$ or $D^2$, and with the proviso that $Q^2$ being polyfunctional is linked to the matrix $M^2$ at one or two sites,
C. contacting a physiological fluid which contains the analyte, a dye and a quencher in vivo with an excitation light source coupled with a detector;
D. producing a detectable and quantifiable signal in the range of about 430 to 800 nm; and
E. determining the concentration of said polyhydroxyl-substituted analyte in said physiological fluid.

In another aspect of the method, the Dye $D^1$ is selected from pyranine derivatives having the structure of:

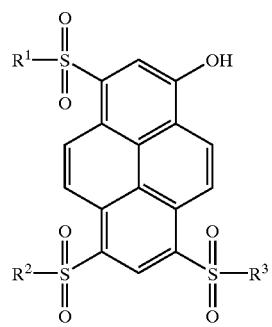

where $R^1$, $R^2$ and $R^3$ are each —NH—$CH_2$—$CH_2$(—O—$CH_2$—$CH_2$)$_n$—$X^1$,
wherein $X^1$ is selected from —OH, —$OCH_3$, —$CO_2H$, —$CONH_2$, —$SO_3H$, or —$NH_2$; and n is between about 70 and 10,000, and preferably between 100 and 1,000.

In another aspect of the method, the Dye $D^2$ is prepared from pyranine derivatives having the structure of:

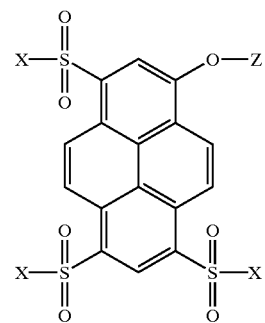

X = Cl, Br or from a dye monomer selected from the group consisting of:

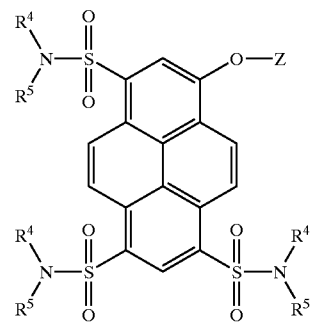

where $R^4$=—H
and
$R^5$ is selected from: —$R^6$—NH—(C=O)—(C=$CH_2$)—$R^7$, —$R^6$—O—(C=O)—(C=$CH_2$)—$R^7$, —$CH_2$—$C_6H_4$—CH=$CH_2$, or —$CH_2$—CH=$CH_2$
where in $R^6$ is a lower alkylene of 2 to 6 carbons and $R^7$=—H, or —$CH_3$
where Z is a blocking group that is removed by hydrolysis selected from:

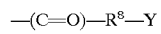

—(C=O)—$R^8$—Y where $R^8$ is a lower alkylene of 1 to 4 carbon atoms and Y is selected from —H, —OH, —$CO_2H$, —$SO_3H$, —(C=O)—NH—$R^9$, or —$CO_2$—$R^9$
where $R^9$ is a lower alkylene of 1 to 4 carbon atoms.

In another aspect of the method, the quencher $Q^1$ or $Q^2$ is prepared from a quencher precursor selected from the group consisting of:

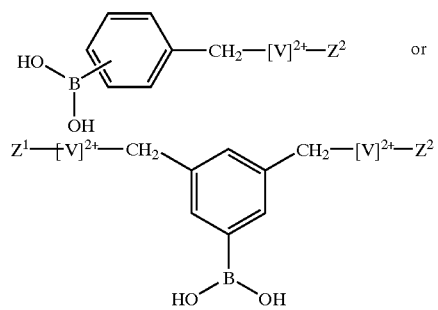

where $(V)^{2+}$ is a nitrogen containing conjugated heterocyclic aromatic group selected from isomers of dipyridyls, dipyridyl ethylenes, dipyridyl phenylenes, phenanthrolines, or diazafluorenes; wherein the two nitrogen atoms are each in a different aromatic ring and the nitrogens are in all positions capable of forming an onium salt and where $Z^1$ or $Z^2$ is either a polymerizable ethylenically unsaturated group selected from:

(i) $-R^{10}-CO_2-C(R^{11})=CH_2$, $-R^{10}-NH-(C=O)-C(R^2)=CH_2$, or $-CH_2-C_6H_4-CH=CH_2$, here $R^{10}$ is a lower alkylene or hydroxyalkylene of 2 to 6 carbon atoms and where $R^{11}=-H$ or $-CH_3$; or (ii) a coupling group selected from: $-R^{12}-Y^1$ where $R^{12}$ is $-CH_2C_6H_4-$ or alkylene of 2 to 6 carbon atoms and Y is $-OH$, $-SH$, $-CO_2H$, or $-NH_2$. $Q^1$ is a pendant group or chain unit in a water-soluble or dispersible polymer (linear or branched). The polymer matrix $M^2-L^2-Q^2$ is preferably a water-insoluble (crosslinked) network polymer.

For the dye D, note that $D^1$ and $D^2$ are defined with the proviso that the dye $D^1$ and $D^2$ do not include a diazo linkage $-N=N-$.

For the quencher Q, $Q^1$ and $Q^2$ are defined with the proviso that the quencher $Q^1$ and $Q^2$ do not include a diazo linkage $-N=N-$.

For the in vivo applications, described herein, the ortho-benzylboronic acid derivatives are excluded.

BRIEF DESCRIPTION OF THE FIGURES

FIGS. 3A to 3D are schematic representations of structures of monomeric quencher precursors:

FIG. 3A is trans-1,2-bis-4-N-(benzyl-4-boronic acid)-4'-N'-(benzyl-4-ethenyl)-dipyridinium4-ethylene dibromide;

FIG. 3B is 1-N-(benzyl-3-boronic acid)-4'-N'-(benzyl-3-ethenyl)-3 phenanthrolinium dibromide;

FIG. 3C is 4-N-(benzyl-3-boronic acid)-4'-N'-(benzyl-4-ethenyl)-dipyridinium bromide chloride (m-SBBV);

FIG. 3D is 4-N-(benzyl-4-boronic acid)-4'-N'-(benzyl-4-ethenyl)-dipyridinium bromide chloride (p-SBBV).

FIG. 5 is a graphic representation of the response of benzyl viologen (0.001 M) and 4,4'-N,N'-bis-(benzyl-3-boronic acid)-dipyridinium dibromide (m-BBV) showing modulation of m-BBV quenching efficiency toward HPTS-PEG ($1\times10^{-5}$ M) as a function of glucose concentration.

DETAILED DESCRIPTION OF THE INVENTION AND PREFERRED EMBODIMENTS

Definitions

Figure 1:
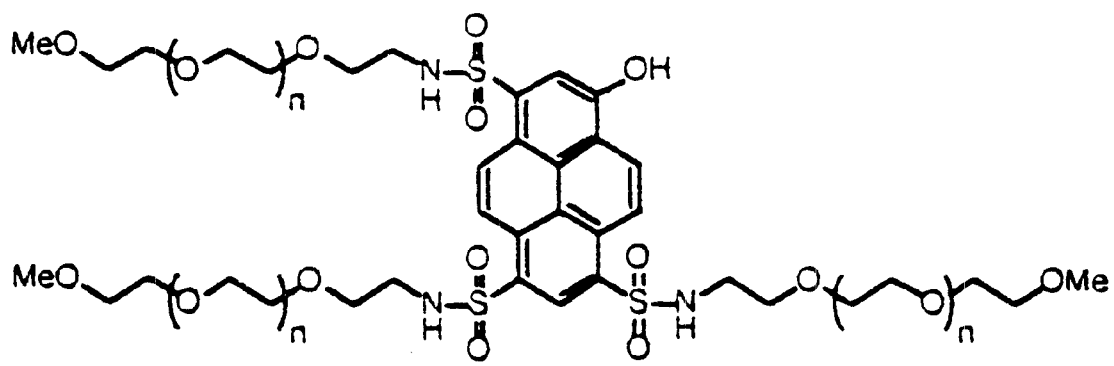
FIG. 1 is the structural formula of N,N',N'-tris-(1-aminoethyl-2-polyethylene glycol (n~125)-methoxy-8-hydroxy-pyrene 1,3,6-tris-sulfonamide) (HPTS-PEG).

As used herein:

"Detector" refers to a device for monitoring light intensity such as a photo diode.

"Fluorophore" or "fluorophore dye" or "dye" refers to a compound that when exposed to light of appropriate wavelength emits light, i.e., it fluoresces.

"HEMA" refers to 2-hydroxyethylmethacrylate.

"Light source" or "excitation light source" refers to a device that emits electromagnetic radiation such as a xenon lamp, medium pressure mercury lamp, a light emitting diode (LED) all of which are commercially available.

"Linking group" refers to $L^1$ or $L^2$ which are divalent moieties, that covalently connect the sensing moiety to the polymer or matrix. Examples of $L^1$ or $L^2$ include those which are each independently selected from a direct bond or, a lower alkylene having 1 to 8 carbon atoms, optionally terminated with or interrupted by one or more divalent connecting groups selected from sulfonamide ($-SO_2NH-$), amide $-(C=O)N-$, ester $-(C=O)-O-$, ether $-O-$, sulfide $-S-$, sulfone ($-SO_2-$), phenylene $-C_6H_4-$, urethane $-NH(C=O)-O-$, urea $-NH(C=O)NH-$, thiourea $-NH(C=S)-NH-$, amide $-(C=O)NH-$, amine $-NR-$ (where R is defined as alkyl having 1 to 6 carbon atoms) and the like.

"Quencher" refers to a compound that reduces the emission of a fluorophore when in its presence.

"In vivo" refers to analysis in a living mammal, preferably a human being.

"IPN" or "interpenetrating polymer network" refers to a combination of two or more network polymers synthesized in juxtaposition (see L. H. Sperling, Interpenetrating Polymer Networks, ACS Advances in Chemistry Series 239, 1994, from Aug. 25–30, 1991 New York ACS Meeting).

"Semi-IPN" or semi-interpenetrating polymer network" refers to a combination of polymers in which one component is soluble and the other polymer is a network (see Sperling above).

"Onium" refers to a heteroaromatic ionic compound having a formal positive charge on the heteroatom, which in the case of viologen is a nitrogen.

"PEG" or "polyethylene glycol" refers to polymer or chain segments which contain oxyethylene ($-OCH_2-CH_2-$) repeating units.

"PEGDMA" refers to polyethylene glycol terminated with two methacrylate groups.

"PEGMA" refers to polyethylene glycol terminated with one methacrylate group.

"Visible light range" refers to light in the spectrum between about 400 and 800 nm.

"Viologen" refers generally to compounds having the basic structure of a nitrogen containing conjugated N-substituted heterocyclic aromatic bis-onium salt, such as 4,4'-N,N bis-(benzyl) bipyridium dihalide (i.e., dichloride), etc.

The present invention concerns a number of important advances. These include but are not limited to an in vivo device for determining carbohydrate, 1,2-diol or 1,3-diol levels in physiological fluid, a series of fluorophore dyes, a series of boronic acid substituted quenchers, and combinations of interacting water-compatible organic polymers. These aspects are discussed in more detail below. The components are discussed first, and their combination to produce the method and the device follows.

Quencher

The moiety that provides glucose recognition in the present invention is an aromatic boronic acid. More specifically, the boronic acid of this invention is covalently bonded to a conjugated nitrogen-containing heterocyclic aromatic bis-onium structure, e.g. a viologen, (see FIG. 3) in which the boronic acid has a pKa less than about 7 for in vivo applications, and reacts reversibly with glucose in aqueous media to form boronate esters. The extent of reaction is related to glucose concentration in the medium.

Bis-onium salts of this invention are prepared from conjugated heterocyclic aromatic dinitrogen compounds. The conjugated heterocyclic aromatic dinitrogen compounds are selected from dipyridyls, dipyridyl ethylenes, dipyridyl phenylenes, phenanthrolines, and diazafluorenes, wherein the nitrogen atoms are in a different aromatic ring and are able to form an onium salt. It is understood that all isomers of said conjugated heterocyclic aromatic dinitrogen compounds in which both nitrogens can be substituted are useful in this invention. Bis-onium salts derived from 4,4'-dipyridyl are preferred. The viologen boronic acid adducts are pendant groups or units in the chain of a water soluble or dispersible polymer with a molecular weight greater than 10,000 or are bonded to an insoluble polymer matrix.

One or more boronic acid groups are attached to the viologen moieties. Representative boronic acid groups include the following:

1. boronic acid substituted viologen of the structure:

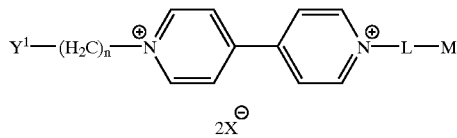

where n=0–3, preferably n is 1, and where L is a linking group, i.e. $L^1$ or $L^2$ and M is a polymer matrix, and where $Y^2$ is phenyl boronic acid (m- and p-isomers) or naphthyl boronic acid, preferably phenyl boronic acid, and 2. as a substituent on the heterocyclic ring of a viologen.

The viologen is contemplated to include combinations of the above. The precursor from which the viologen/boronic acid is derived is an unsymmetrically substituted viologen, such as with a boronic acid functional group on one end and a polymerizable group, such as a vinyl group, on the other (see FIGS. 3A–3D). The viologen/boronic acid moiety is a pendant group or a chain unit in a water soluble or dispersible polymer, or a unit in a crosslinked, hydrophilic polymer or hydrogel sufficiently permeable to glucose to allow equilibrium to be established.

Fluorophore Dye

Figure 2:
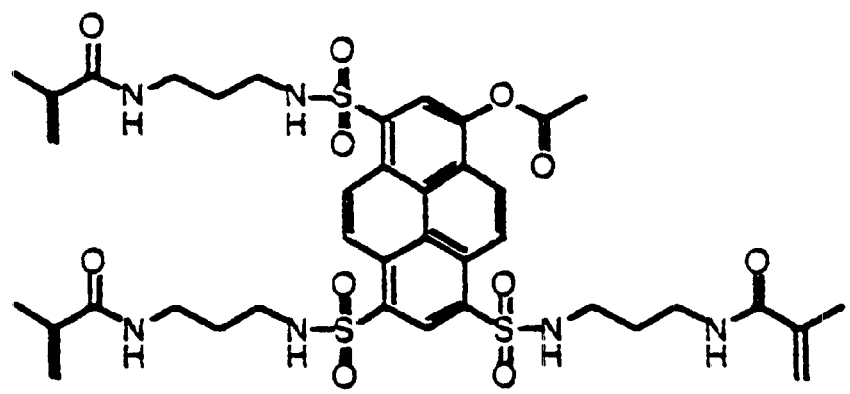
FIG. 2 is the structural formula of N,N',N"-tris-(1-aminopropyl-3-methacrylamide)-8-acetoxy-pyrene-1,3,6-tris-sulfonamide (acetoxy-HPTS-MA).

Dyes useful in this invention (See FIGS. 1 and 2) are excited by light of wavelength about or greater than 430 nm, with a Stokes shift large enough that the excitation and emission wavelengths are separable, by at least 10 nm, and preferably greater than or equal to about 30 nm. These dyes are susceptible to quenching by electron acceptor molecules, such as viologens, are resistant to photo-bleaching, and are stable against photo-oxidation, hydrolysis, and biodegradation. Dyes useful in the present invention have an apparent Stern-Volmer quenching constant when tested with methyl viologen of about 50 or greater and preferably greater than 100. A general description of the Stern-Volmer test is found below in Preparation A. Preferred dyes include polymeric derivatives of hydroxypyrene trisulfonic acid. In some cases, the dye is bonded to a polymer through the sulfonamide functional groups. The polymeric dyes are water-soluble, water-insoluble but swellable or dispersible in water or may be crosslinked. A preferred dye as a polymer is for example, a water soluble PEG adduct N,N',N"-tris-(1-aminoethyl-2-polyethylene glycol (n~125)-methoxy-8-hydroxypyrene 1,3,6-tris-sulfonamide formed by reaction of acetoxypyrene trisulfonyl chloride with amino PEG monomethyl ether. The resulting dye polymer has a molecular weight of at least about 10,000 such that, when it is trapped in a hydrogel or network polymer matrix, it is incapable of diffusing out of the matrix into the surrounding aqueous medium. Other examples include soluble copolymers of N,N',N"-tris-(1-aminopropyl-3-methacrylamide)-8-acetoxy-pyrene-1,3,6-tris-sulfonamide with HEMA, PEGMA, or other hydrophilic comonomers. The phenolic substituent in the dye is protected during polymerization by a blocking group that can be removed by hydrolysis after completion of polymerization. Such blocking groups which are suitable for example acetoxy, trifluoroacetoxy, and the like are well known in the art.

It is essential that, for sensing to occur, the sensing moieties (analyte, dye, quencher) must be in close physical proximity to allow interaction, i.e. mixed on a molecular level and in equilibrium with the species to be detected. While not bound by any theory or mechanism, in most cases the molecules may have to collide or the molecule centers are less than 10 angstroms apart for quenching to occur. However the distance dependent quenching falls of rapidly if the molecules are further apart. It appears that the intensity of the fluorescence emitted by the dye is attenuated by photo-induced intermolecular electron transfer from dye to viologen when viologen/boronic acid adduct and the dye are in close proximity. When glucose binds to the boronic acid, the boronate ester interacts with the viologen thereby altering its quenching efficacy according to the extent of glucose binding. The specific nature of this interaction is not yet established, but it may involve electron transfer from boronate to viologen or boronate formation may shift the reduction potential of the viologen. The reduction potential is an indicator of the ability of a quencher to accept an electron.

Polymer Matrix for Sensors

In in vivo, the sensor is used in a moving stream of physiological fluid which contains one or more polyhydroxyl organic compounds. Thus, for use in vivo, the sensing components are part of an organic polymer sensing assembly. Therefore, it is essential that none of the sensing moieties escape from the polymer assembly. Soluble dyes and quenchers can be confined by a semi-permeable membrane that allows passage of the analyte but blocks passage of the sensing moieties. This can be realized by using as sensing moieties soluble molecules that are substantially larger (molecular weight greater than 1000 preferably greater than 5000) than the analyte molecules; and employing a dialysis or an ultrafiltration membrane with a specific molecular weight cutoff between the two so that the sensing moieties are quantitatively retained.

Figure 8:
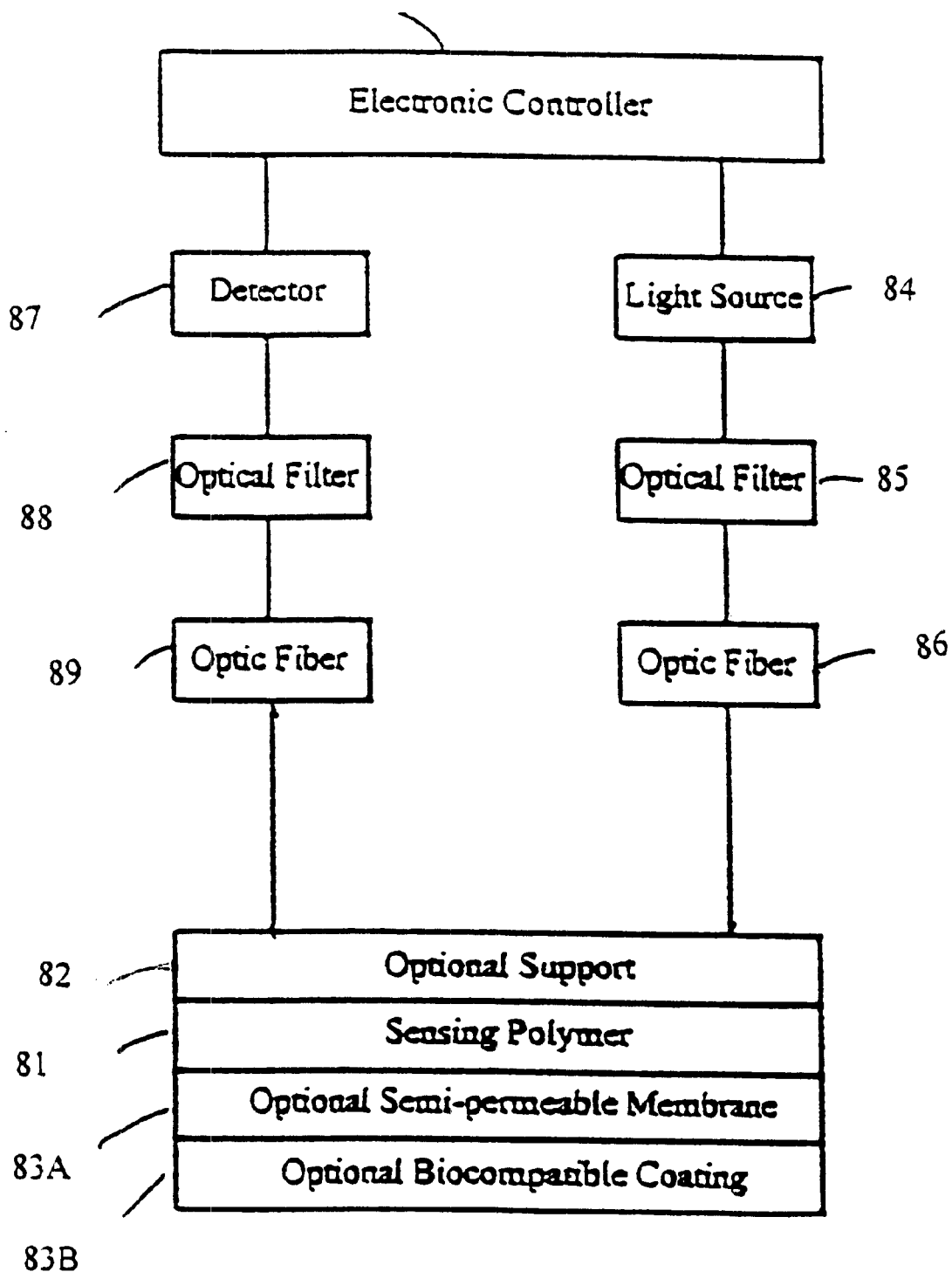
FIG. 8 is a schematic representation of one embodiment illustrating the use of the sensing polymer assembly.

Preferably, the sensing moieties are immobilized in an insoluble polymer matrix which is freely permeable to glucose see FIG. 8. The polymer matrix is comprised of organic, inorganic or combinations of polymers thereof. The matrix may be composed of biocompatible materials. Alternatively, the matrix is coated with a second biocompatible polymer that is permeable to the analytes of interest. The function of the polymer matrix is to hold together and immobilize the fluorophore and quencher moieties while at the same time allowing contact with the analyte, and binding of the analyte to the boronic acid. To achieve this effect, the matrix must be insoluble in the medium, and in close association with it by establishing a high surface area interface between matrix and analyte solution. For example, an ultra-thin film or microporous support matrix is used. Alternatively, the matrix is swellable in the analyte solution e.g. a hydrogel matrix is used for aqueous systems. In some instances, the sensing polymers are bonded to a surface such as the surface of a light conduit, or impregnated in a microporous membrane. In all cases, the matrix must not interfere with transport of the analyte to the binding sites so that equilibrium can be established between the two phases. Techniques for preparing ultra-thin films, microporous polymers, microporous sol-gels, and hydrogels are established in the art.

Hydrogel polymers are preferred for this invention. The term, hydrogel, as used herein refers to a polymer that swells substantially, but does not dissolve in water. Such hydrogels may be linear, branched, or network polymers, or polyelectrolyte complexes, with the proviso that they contain no soluble or leachable fractions. Typically, hydrogel networks are prepared by a crosslinking step which is performed on water soluble polymers so that they swell but do not dissolve in aqueous media. Alternatively, the hydrogel polymers are prepared by copolymerizing a mixture of hydrophilic and crosslinking monomers to obtain a water swellable network polymer. Such polymers are formed either by addition or condensation polymerization, or by combination process. In these cases, the sensing moieties are incorporated into the polymer by copolymerization using monomeric derivatives in combination with network-forming monomers. Alternatively, reactive moieties are coupled to an already prepared matrix using a post polymerization reaction. Said sensing moieties are units in the polymer chain or pendant groups attached to the chain.

The hydrogels useful in this invention are also monolithic polymers, such as a single network to which both dye and quencher are covalently bonded, or multi-component hydrogels. Multi-component hydrogels include interpenetrating networks, polyelectrolyte complexes, and various other blends of two or more polymers to obtain a water swellable composite which includes dispersions of a second polymer in a hydrogel matrix and alternating microlayer assemblies.

Monolithic hydrogels are typically formed by free radical copolymerization of a mixture of hydrophilic monomers, including but not limited to HEMA, PEGMA, methacrylic acid, hydroxyethyl acrylate, N-vinyl pyrrolidone, N,N'-dimethyl acrylamide, and the like; ionic monomers include methacryloylaminopropyl trimethylammonium chloride, diallyl dimethyl ammonium chloride, vinyl benzyl trimethyl ammonium chloride, sodium sulfopropyl methacrylate, and the like; crosslinkers include ethylene dimethacrylate, PEGDMA, trimethylolpropane triacrylate, and the like. The ratios of monomers are chosen to optimize network properties including permeability, swelling index, and gel strength using principles well established in the art. In one embodiment, the dye moiety is an ethylenically unsaturated derivative of a dye molecule, such as N,N'N''-tris-(1-aminopropyl-3-methacrylamide)-8-acetoxy-pyrene-1,3,6-tris-sulfonamide, the quencher moiety is an ethylenically unsaturated viologen such as 4-N-(benzyl-3-boronic acid)-4'-N'-(benzyl-4-ethenyl)-dipyridinium dihalide (m-SBBV) and the matrix is made from HEMA and PEGDMA. The concentration of dye is chosen to optimize emission intensity. The ratio of quencher to dye is adjusted to provide sufficient quenching to produce the desired measurable signal.

Alternatively, a monolithic hydrogel is formed by a condensation poymerization. For example, acetoxy pyrene trisulfonyl chloride is reacted with an excess of PEG diamine to obtain a tris-(amino PEG) adduct dissolved in the unreacted diamine. A solution of excess trimesoyl chloride and an acid acceptor is reacted with 4-N-(benzyl-3-boronic acid)-4'-N'-(2-hydroxyethyl) bipyridinium dihalide to obtain an acid chloride functional ester of the viologen. The two reactive mixtures are brought into contact with each other and allowed to react to form the hydrogel, e.g. by casting a thin film of one mixture and dipping it into the other.

Polymers that are capable of reacting with boronic acids to form boronate esters under the conditions of this method are not useful as matrix polymers. Such polymers have 1,2- or 1,3-dihydroxy substituents, including but not limited to cellulosic polymers, polysaccharides, polyvinyl alcohol and its copolymers and the like.

Multi-component hydrogels wherein the dye is incorporated in one component and the quencher in another are preferred for making the sensor of this invention. Further, these systems are optionally molecularly imprinted to enhance interaction between components and to provide selectivity for glucose over other polyhydroxy analytes. Preferably, the multi-component system is an interpenetrating polymer network (IPN) and most preferably a semi-interpenetrating polymer network (semi-IPN).

The IPN polymers are typically made by sequential polymerization. First, a network comprising the quencher is formed. The network is then swollen with a mixture of monomers including the dye monomer and a second polymerization is carried out to obtain the IPN hydrogel.

The semi-IPN hydrogel is formed by dissolving a soluble polymer containing dye moieties in a mixture of monomers including a quencher monomer and polymerizing. Alternatively, a soluble quencher polymer is dissolved in a monomer mixture containing the dye monomer and the mixture polymerized. In either case, the molecular weight of the soluble component must be sufficiently high (about or greater than 10,000) that it cannot diffuse out of the network, i.e. it becomes physically bound in or trapped by the matrix.

Figure 4B:
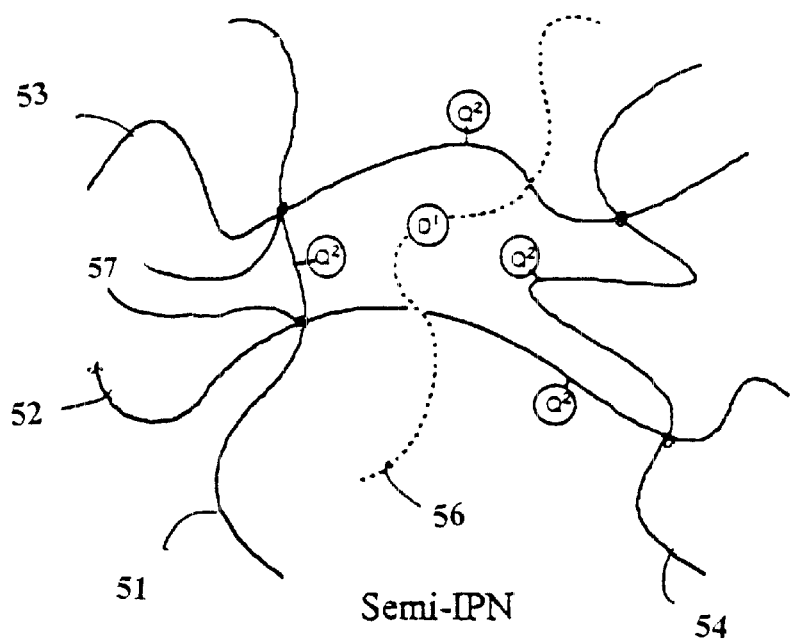
FIGS. 4A and 4B are schematic representations of the structures of the interpenetrating polymer network (IPN) and semi-IPN polymers respectively of the invention.
Figure 4A:
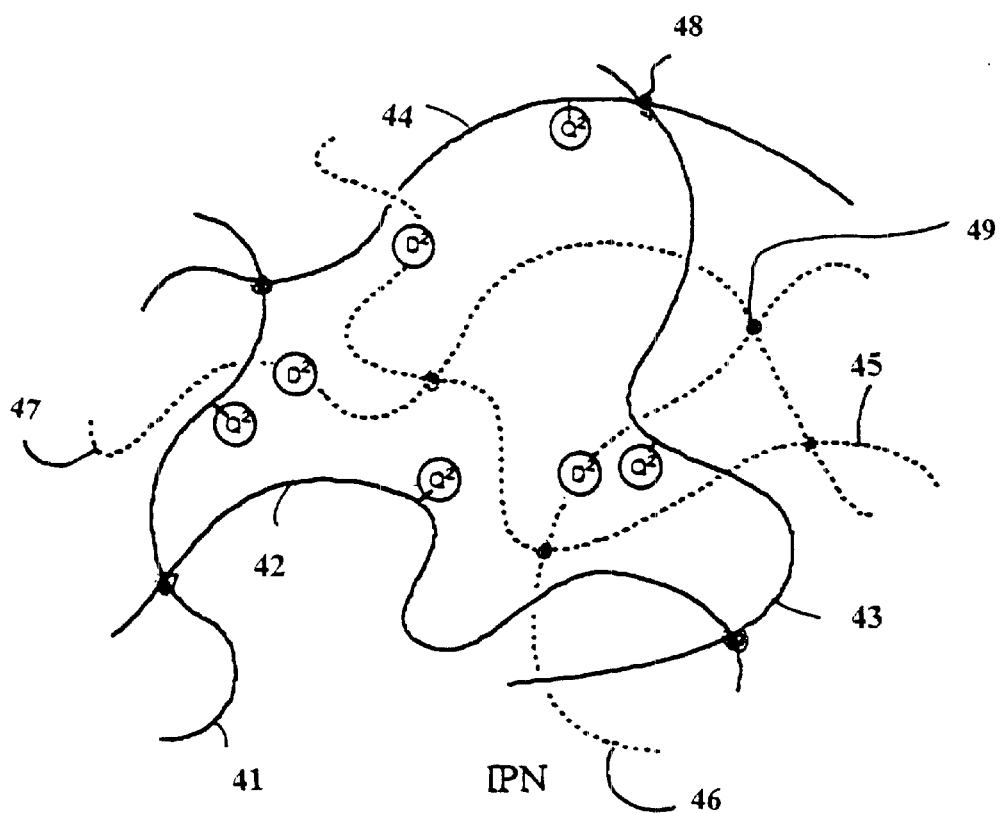
Figure 6:
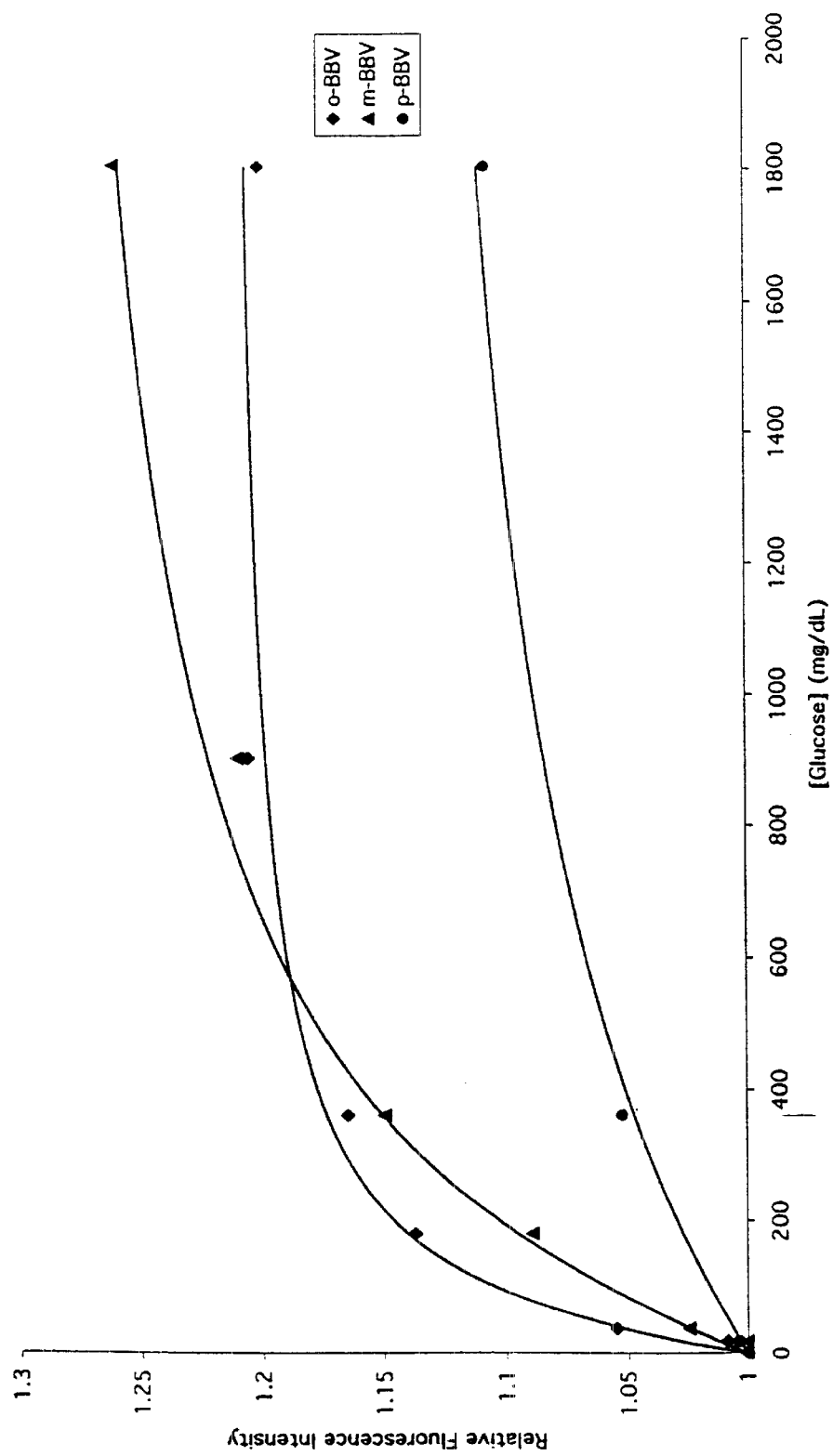
FIG. 6 is a graphic representation of the response of ortho-, meta-, and para-benzyl boronic acid viologen (BBV) (0.001M) showing modulation of quenching efficiencies to HPTS-PEG ($1\times10^{-5}$ M) as a function of glucose concentration.

In FIG. 4A, one group of polymer chains 41, 42, 43 and 44 contain the quencher, for example quencher $Q^2$. A second group of polymer chains 45, 46 and 47 containing the dye, for example, dye $D^2$, is formed at about the same time or sequentially. The points of crosslinking of the polymers are designated as 48 and 49. In FIG. 4B, one group of polymer chains 51, 52, 53 and 54 contain the quencher, for example, quencher $Q^2$. Dye $D^1$ is covalently bound to a second polymer 56. Crosslinking points 57 are designated.

The individual components in a multi-component hydrogel are made by the same or a different polymerization scheme. For example, in an IPN polymer, a first network is formed by free radical polymerization, the second by condensation polymerization. Likewise, in a semi-IPN polymer, the soluble component is formed by condensation polymerization and the network by free radical polymerization. For example, a quencher polymer, such as poly 4,4'-N,N'-bis(1,3-xylylene-5-boronic acid) bipyridinium dihalide is formed by condensing 4,4'-dipyridyl with 3,5-bis-bromomethyl phenylboronic acid. The quencher polymer is dissolved in a reaction mixture containing N N',N"-tris-(1-aminopropyl-3-methacrylamide)-8-acetoxy-pyrene-1,3,6-tris-sulfonamide as is described above, and the solution is polymerized to obtain the semi-IPN hydrogel.

The combination of components described herein produces a device for the determination of polyhydroxy substituted organic molecules in physiological fluids.

In a specific embodiment a high molecular weight water-soluble dye is prepared by condensing acetoxypyrene trisulfonyl chloride with aminoethyl PEG monomethyl ether to obtain the N,N,',N"-tris-(1-aminoethyl-2-polyethylene glycol (n~125)-methoxy-8-hydroxypyrene 1,3,6-tris-sulfonamide). The PEG dye polymer is dissolved in a mixture comprised of HEMA, PEGDMA, 4-N-(benzyl-3-boronic acid)-4'-N'-(benzyl-4-ethenyl)-dipyridinium dihalide (m-SBBV), aqueous alcohol and free radical initiator and polymerized to obtain a semi-IPN hydrogel. After hydrolysis with dilute base and leaching with deionized water, the hydrogel is affixed to a bifurcated optical fiber light conduit such that it can be exposed to and equilibrate with the body fluid. The light conduit together with appropriate filters is connected to a blue light emitting diode (LED) light source and a silicon photodetector together with an electronic controller and associated measurement instrumentation. The sensor is placed in the tip of a catheter which is inserted in the body in the desired location. The sensor is excited by light of about 475 nm and the fluorescence intensity monitored at about 520 nm. The level of glucose in the body fluid is determined from the intensity of the emission.

A Single Component Viologen Sensor

In another embodiment the invention is a boronic acid substituted viologen covalently bonded to a fluorophore. Preferably the adduct is a polymerizable compound or is a unit in a polymer. One such adduct is prepared by first forming an unsymmetrical viologen from 4,4' dipyridyl by attaching a benzyl-3-boronic acid group to one nitrogen and an aminoethyl group to the other. The viologen is condensed sequentially first with 8-acetoxy-pyrene-1,3,6-trisulfonyl chloride in a 1:1 mole ratio followed by reaction with excess PEG diamine to obtain a prepolymer mixture. An acid acceptor is included in both steps to scavange the byproduct acid. The prepolymer mixture is crosslinked by reaction with a polyisocyanate to obtain a hydrogel. The product is treated with base to remove the blocking group. Incomplete reaction products and unreacted starting materials are leached out of the hydrogel by exhaustive extraction with deionized water before further use. The product is responsive to glucose when used as the sensing component as described herein.

Alternatively, said adducts are ethylenically unsaturated monomers for example dimethyl bis-bromomethyl benzene boronate is reacted with excess 4,4'-dipyridyl to form a half viologen adduct. After removing the excess dipyridyl, the adduct is further reacted with an excess of bromoethylamine hydrochloride to form the bis-viologen adduct. This adduct is coupled to a pyranine dye by reaction with 8-hydroxypyrene trisulfonyl chloride in a 1:1 mole ratio in the presence of an acid acceptor followed by reaction with excess aminopropylmethacrylamide. Finally, any residual amino groups are reacted with methacrylol chloride. After purification the dye/viologen monomer is copolymerized with HEMA and PEGDMA to obtain a hydrogel.

The advantage of this group of viologens is that dye and quencher are held in close proximity by covalent bonds which could lead to increased sensitivity. The disadvantage is that making these adducts is a formidable synthetic challenge and changes in composition are difficult to imlement. Characterization and purification of the product is equally difficult. Therefore, the embodiments in which dye and quencher are separate entities are preferred.

Device Configuration

FIG. 8 is a schematic representation of the device as used for one time or continuous monitoring for sugar, i.e. glucose. The sensing polymer 81 which contains the dye and quencher may be attached to an optional support 82. For some embodiments an optional semi-permeable polymer membrane 83A is present. For other applications it may be useful to have an optimal biocompatible coating 83B covering the assembly. The light source 84 is connected to an optical filter 85 to an optical fiber 86 to the sensing polymer 81. Detector 87 is connected to an optical filter 88 to an optical fiber 89 which connects to sensing polymer 81. Light source 84 and detector 87 are both connected to electronic controller 90. Thus the system can detect changes in the sensing polymer based on the glucose content of the physiological fluid.

Figure 10:
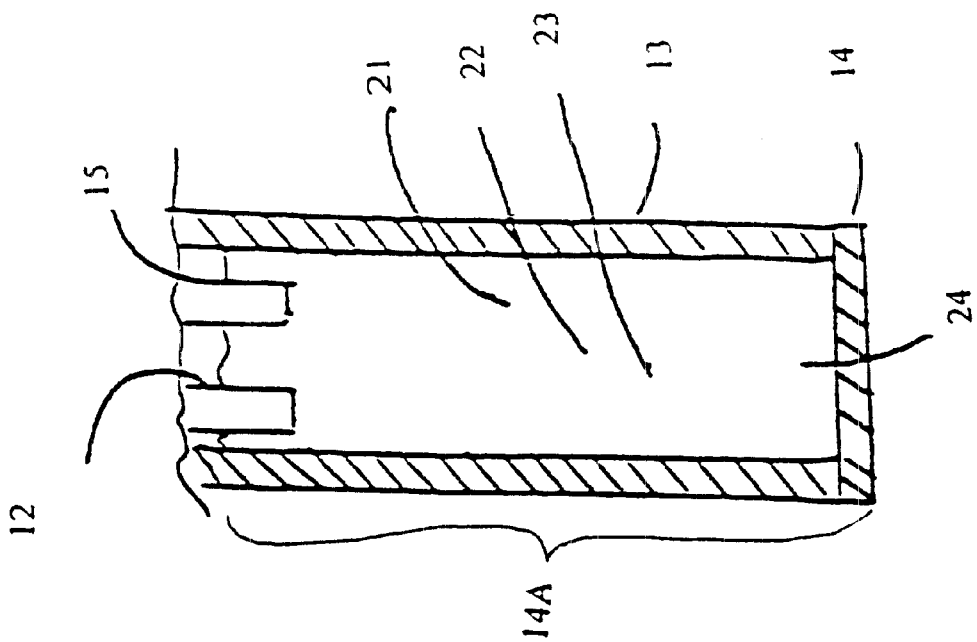
FIG. 10 is a schematic cross-sectional representation of the in vivo sensing polymer assembly of FIG. 9.
Figure 9:
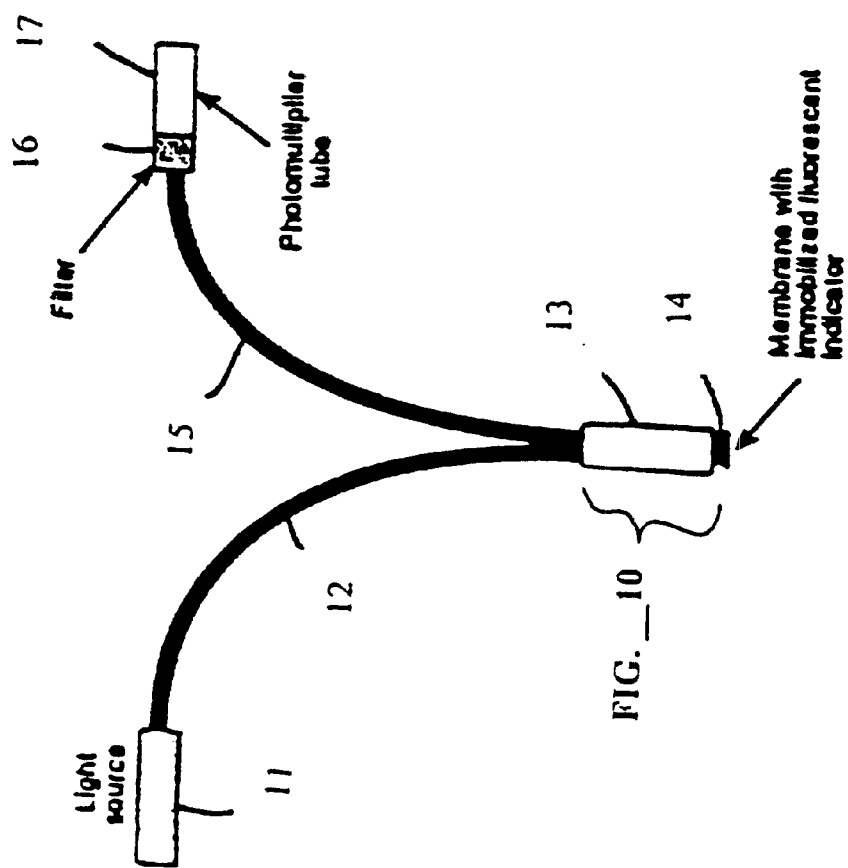
FIG. 9 is a schematic representation of a second embodiment of the implanted sensor as it would be used to monitor in vivo for polyhydroxyl organic compounds, i.e. glucose or fructose.

The device useful in a process stream and for in vivo implanting and monitoring is shown in FIGS. 9 and 10. FIG. 9 shows the optical device. FIG. 10 is the cross sectional representation of the probe. For FIG. 9, light source 11 (visible) is connected by optical fiber 12 to active cell 13. Semipermeable membrane 14 allows the analyte to enter and exit freely from cell 13. Optical fiber 15 conveys the altered light to filter 16, and optional photomultiplier to 17 to produce the analyte spectrum for analysis.

As shown in FIGS. 9 and 10, cell 13 includes the selectively permeable membrane such that the mixture of polymer 21, dye 22, and quencher 23 are retained in cell 13 under the conditions of analysis. The light enters cell 14 via optical fiber 12. Within the active portion of 14A of cell 14, the polymer 21, dye 22 and quencher 33 contact analyte 24 which has selectively entered the cell causing a quantitative and reporducible change in the spectrum. This modified light signal travels optical fiber 15 to photomultiplier 17 to be analyzed.

Experimental

Reagents and solvents are used as received from commercial supplier unless otherwise noted. (See *Chem Sources USA* which is published annually.)

The following be examples are provided to be descriptive and exemplary only. They not to be construed to limiting in any manner or fashion.

The Preparations, Procedures, Comparative Examples and Examples below describe this invention. In some cases the Preparations are described as Examples in the comparison patent application. U.S. Ser. No. 09/731,325, filed on Dec. 5, 2000 by Express Mail Certificate EL749298972US, which is incorporated herein by reference in its entirety.

Procedure A

Fluorescence Spectroscopy Analysis of the Apparent Stern-Volmer Quenching Constant of Methyl Viologen with a Fluorescent Dye The apparent Stern-Volmer quenching constant is derived from the slope of a Stern-Volmer plot of relative fluorescence intensity ($F_o/F$) versus concentration of quencher (M). See J. R. Lakowicz, (1999) *Principles of Fluorescence Spectroscopy Second Edition,* Kluwer Academic/Plenum Publishers, New York, pp. 237–289. One skilled in the art is in general able to perform this analysis for any fluorescent dye/quencher pair in a particular solvent of interest. This general Stern-Volmer analysis is used in determining the Stern-Volmer quenching constants in 0.1 ionic strength pH 7.4 phosphate buffer.

In order to avoid concentration quenching effects, the concentration of the dye is generally adjusted so that the optical density of the dye, at excitation $\lambda_{max} \leq 0.5$ absorption units. Once the desired dye concentration is determined, a stock dye solution is prepared in which the concentration is 5 times greater than that desired in the final measurements. For example, a dye for which the desired final concentration, which gives an optical density of excitation $\lambda_{max} \leq 0.5$ absorption units, is $1 \times 10^{-5}$ M, would require a stock solution in which the concentration is $5 \times 10^{-5}$ M.

Once determined, as is described above, 10 mL of dye stock solution of the appropriate concentration is made by weighing out the appropriate mass of dye and placing the solid into a 10 mL volumetric flask. The flask is then filled to the 10 mL mark with 0.1 ionic strength pH 7.4 phosphate buffer.

A stock solution of methyl viologen (25 mL, 0.0025 M) was prepared in a 10-mL volumetric flask with pH 7.4 phosphate buffer (0.1 ionic strength). Seven different solutions containing methyl viologen were then prepared in pH 7.4 phosphate buffer as described below in Table 1:

TABLE 1

| Volume dye standard (mL) | Volume quencher standard (mL) | Volume buffer (mL) | Final (dye) (M) | Final (Quencher) (M) |
| --- | --- | --- | --- | --- |
| 1 | 0.00 | 4.00 | 1.00E−05 | 0.00E+00 |
| 1 | 0.20 | 3.80 | 1.00E−05 | 1.00E−04 |
| 1 | 0.30 | 3.70 | 1.00E−05 | 1.50E−04 |
| 1 | 0.50 | 3.50 | 1.00E−05 | 2.50E−04 |
| 1 | 1.00 | 3.00 | 1.00E−05 | 5.00E−04 |
| 1 | 1.50 | 2.50 | 1.00E−05 | 7.50E−04 |
| 1 | 2.00 | 2.00 | 1.00E−05 | 1.00E−03 |

Each sample is then in-turn analyzed in a luminescence spectrometer set at the appropriate excitation wavelength and the appropriate emission wavelength range for the corresponding dye. The instrumental settings (slit widths, scan speed, optical filters, excitation wavelength, emission wavelength range) are held constant throughout the analysis of the series of samples). The emission fluorescence intensity is then determined as the integration of the fluorescence intensity over the emission wavelength range by the trapezoidal rule approximation method. The integrated values are plotted on the y-axis and the quencher concentrations are plotted on the x-axis and the slope of the resulting line is calculated by linear regression as the Stern-Volmer quenching constant. One skilled in the art will realize that based on quenching mechanism the Stern-Volmer plot may not result in a linear relationship. However through the use of the appropriate mathematical relationships, which is known and understood by one skilled in the art, the apparent Stern-Volmer quenching constant is calculated and used for comparison.

Preparation A

Synthesis of Dimethyl-(4-bromomethyl)-benzeneboronate

An oven-dried, 100-mL round bottom flask was cooled under argon, fit with a magnetic stir bar, and charged with (4-bromomethyl)-benzeneboronic acid (12.49 mmols, 2.684 g). The flask was sealed with a septum and charged with pentane (55 mL). The suspension was stirred at room temperature and upon addition of freshly distilled $CH_3OH$ (3.16 g, 4 mL, 97 mmols) the solution instantly clarified. After stirring for 20 minutes, the solution was dried over $MgSO_4$, then over $CaCl_2$ (to remove excess methanol). The supernatant was cannulated, under argon, through a glass-fritted funnel (medium), and the pentane subsequently removed in vacuo. The remaining yellow oil was further dried under reduced pressure (0.1 torr, 1 hr). Yield: 1.6 g, 6.59 mmols (56%). $^1$H-NMR ($CD_3OD$, ppm): 4.5 (s, 2H), 7.4 (d, 2H), 7.55 (d, 2H). $^{11}$B-NMR (MeOH, ppm): 29 (s). Similar procedures were used to prepare the 2- and 3-isomers.

The products were used to make the boronic acid-viologen compounds of Examples 1 and 2.

Preparation B

Synthesis of 8-acetoxy-pyrene-1,3,6-trisulfonyl chloride

Trisodium-8-acetoxy-pyrene-1,3,6-trisulfonate (acetoxy-HPTS, 11.33 g, 20 mmol) was suspended in 30 mL of thionyl chloride to which 5 drops of dimethylformamide was added. The suspension was refluxed for 3 hr., during which time it became a brown solution. The solution was then cooled to 25° C. under an argon atmosphere. Thionyl chloride was then distilled off under vacuum (2 Torr) leaving a yellow residue. The yellow residue was transferred to three separate centrifuge tubes along with 60 mL of dichloromethane. The suspensions were then centrifuged and the supernatant solutions transferred to a dry round bottom flask. The residue remaining in the centrifuge tubes was washed an additional four times each with 10 mL portions of dichloromethane. The supernatant solutions were combined and left overnight under an argon atmosphere and some precipitation was observed. The dichloromethane solution was added to 250 mL of pentane causing precipitation of a large amount of yellow solid. The supernatant was removed by a double ended needle and the yellow solid was dried on high vacuum (0.2 Torr). Yield: 8.62 g, 15.5 mmol (78%), $^1$H-NMR (500 MHz, $CDCl_3$, ppm): 2.682 (s, 3H), 8.833, (d, J=10 Hz, 1H), 8.915 (s, 1H), 9.458 (d, J=10 Hz, 1H), 9.509 (d, J=10 Hz, 1H), 9.630 (s, 1H), 9.685 (d, J=10 Hz, 1H). This product was used in Examples 3 and 5.

Preparation C

Synthesis of 4-(4-pyridyl)-N-(benzyl-4-ethenyl)-pyridinium chloride

An oven-dried, 100-mL round bottom flask was cooled under argon, fit with a magnetic stir bar, and charged with 4,4'-dipyridyl (12.50 g, 80 mmols). The flask was sealed with a septum and charged with $CH_3OH$ (20 mL). The homogenous solution was stirred at room temperature while 4-(chloromethyl)styrene (2.82 mL, 20 mmols) was added dropwise via syringe. After stirring the solution at room temp for 48 hours, the solvent was removed in vacuo. Dry tetrahydrofuran (50 mL) was added to the reaction flask via cannula and the mixture stirred for three days, at which point the stirring was stopped, the solids allowed to settle, and the solvent was removed as much as possible via cannula. This process was repeated two more times, in each case reducing the mixing time to 24 hours. After the third trituration the mixture was filtered under nitrogen and washed with dry diethyl ether (200 mL) via cannula. The cake was dried by passing dry nitrogen through it under pressure for 1 hour, and finally by applying vacuum (0.1 torr, 1 h). Yield: 5.56 g, 18 mmols (90%), $^1$H-NMR (D$_2$O, ppm); 9.12 (d, 2H), 8.86, (d, 2H), 8.48 (d, 2H), 7.98 (d, 2H), 7.67 (d, 2H), 7.57 (d, 2H), 6.87 (dd, 1H), 5.92 (s, 2H), 5.45 (d, 1H). This compound was used in Examples 6 and 7.

COMPARATIVE EXAMPLE A

Synthesis and Evaluation of 4,4-N,N'-bis-(benzyl-3-boronic acid) dipyridinium dibromide An oven-dried, 50-mL centrifuge tube was cooled under argon, fit with a magnetic stir bar, and charged with 4,4'-bipyridyl (0.469 g, 3 mmols). The tube was sealed with a septum and charged with CH$_3$OH (7 mL). The homogenous solution was stirred at room temperature while freshly prepared dimethyl-(3-bromomethyl) benzeneboronate (1.82 g, 7.5 mmols) was added via syringe. After stirring the solution for 15 hours the reaction vessel was centrifuged (4 min at 3200 RPM) and the CH$_3$OH cannulated to a separate flask. The remaining yellow solid was triturated with acetone:water (24:1 V/V, 25 mL), stirred vigorously on a vortex mixer and centrifuged. The acetone solution was removed by cannula and the trituration process repeated two more times. The solid was then triturated with diethylether using the same process. The pale yellow solid, in the centrifuge tube, was then dried on the high vacuum (0.6 torr, 2 hr). Yield: 0.956 g, 1.63 mmols (54%). MP: decomposition>230° C. $^1$H-NMR (D$_2$O, ppm): 6.093 (s, 4H), 7.715, (dd, 2H, J$_1$=7.5 Hz, J$_2$=7.5 Hz), 7.788 (d, 1H, J=7.5 Hz), 7.984 (s, 1H), 8.002 (d, 1H, J=7.5 Hz), 8.662 (d, 4H, J=7 Hz), 9.293 (d, 4H, J=7 Hz). $^{11}$B-NMR (CH$_3$OH, ppm): 29 (s).

This was used for fluorescence spectroscopy analysis with HPTS-PEG. A stock solution of HPTS-PEG (10 mL, 5×10$^{-5}$ M) was prepared in a 10-mL volumetric flask with pH 7.4 phosphate buffer (0.1 ionic strength). Similarly, a m-BBV solution (25 mL, 0.00025 M) was prepared. Seven different solutions containing HPTS-PEG and m-BBV were then prepared in pH 7.4 phosphate buffer as described below in Table 2.

TABLE 2

| Volume HPTS-PEG standard (M) | Volume m-BBV standard (mL) | Final buffer (mL) | Volume (HPTS-PEG) (M) | Final (m-BBV) (M) |
|---|---|---|---|---|
| 1 | 0.00 | 4.00 | 1.00E−05 | 0.00E+00 |
| 1 | 0.20 | 3.80 | 1.00E−05 | 1.005−04 |
| 1 | 0.30 | 3.70 | 1.00E−05 | 1.505−04 |
| 1 | 0.50 | 3.50 | 1.00E−05 | 2.505−04 |
| 1 | 1.00 | 3.00 | 1.00E−05 | 5.005−04 |
| 1 | 1.50 | 2.50 | 1.00E−05 | 7.505−04 |
| 1 | 2.00 | 2.00 | 1.00E−05 | 1.005−03 |

Figure 7:
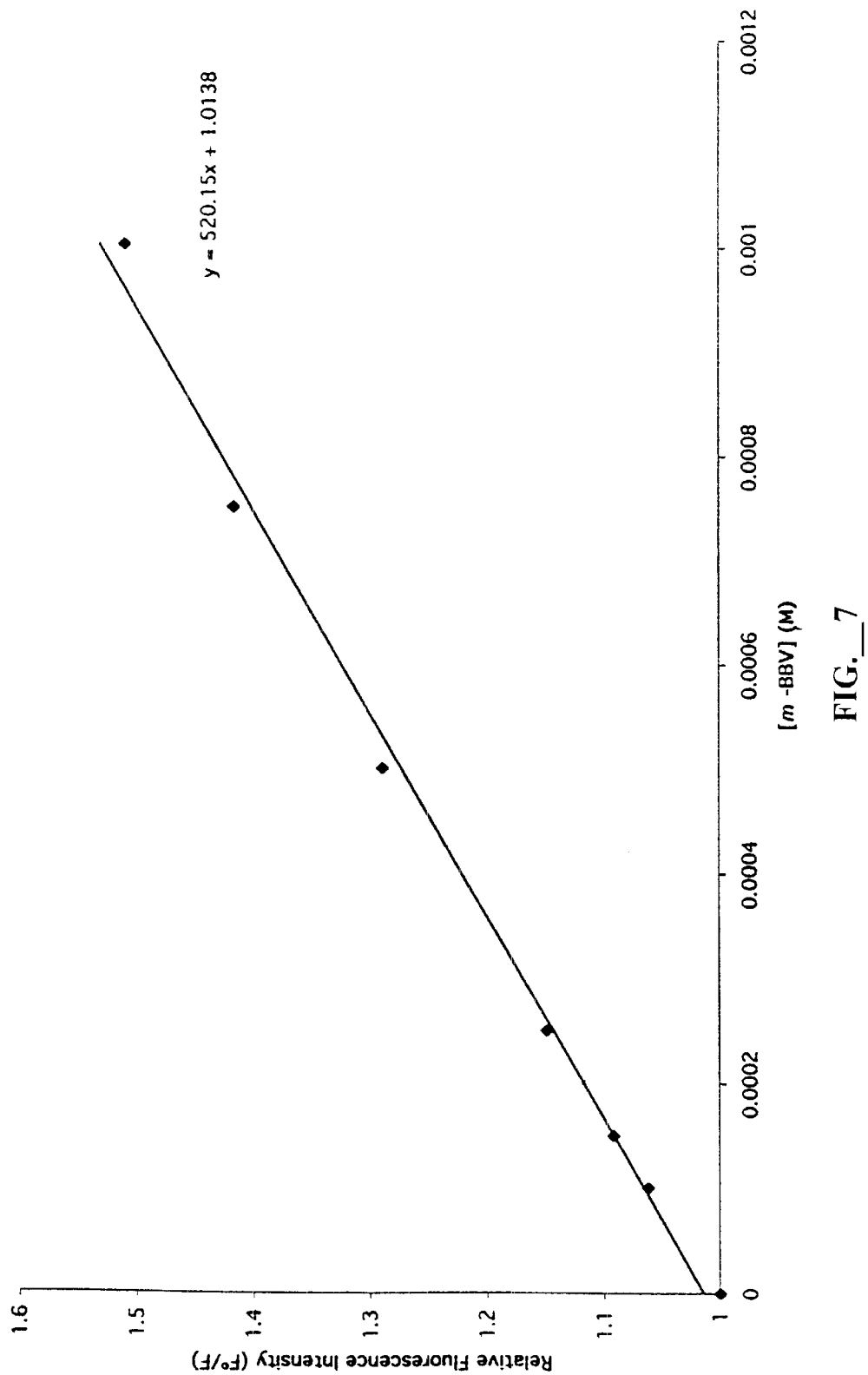
FIG. 7 is a Stern-Volmer plot of m-BBV quenching of HPTS-PEG in pH 7.4 phosphate buffer.

Each sample was then analyzed on the the Perkin-Elmer L550-B luminescence spectrometer. The instrumental settings were:

Excitation Wavelength—473 run
Emission Wavelength Range—480–630 nm
Excitation Slit Width—0 run (Instrumental dependent minimum)
Emission Slit Width—0 run (Instrumental dependent minimum)
Optical filter—none
Scan Speed—100 nm/sec The instrumental settings (slit widths, scan speed optical filters, excitation wavelength, emission wavelength range) were held constant throughout the series analysis. The emission fluorescence intensity was then quantified by integration (the trapezoidal rule approximation method) of the fluorescence intensity curve between 480 and 630 nm. The relative integrated values, were then used to construct a calibration curve: plotting F$_0$/F vs. m-BBV concentration (M), where F$_0$ is the integrated fluorescence intensity of the first sample in Table 2 containing 0 M m-BBV. The apparent Stern-Volmer quenching constant was determined to be 520 M$^{-1}$ (see FIG. 7).

COMPARATIVE EXAMPLE B

Synthesis and Evaluation of 4,4'-N,N'-bis-(benzyl-4-boronic acid)-dipyridinium dibromide An oven-dried, 50-mL centrifuge tube was cooled under argon, fit with a magnetic stir bar, and charged with 4,4'-dypyridyl (0.234 g, 1.5 mmols). The tube was sealed with a septum and charged with anhydrous CH$_3$OH (7 mL). The homogenous solution was stirred at room temperature while freshly prepared dimethyl-(4-bromomethyl)-benzeneboronate (1.09 g, 4.5 mmols) was added via syringe. After stirring the solution for 15 hours, the reaction vessel was centrifuged (4 mm at 3200 RPM) and the CH$_3$OH cannulated to a separate flask. The remaining yellow solid was triturated with acetone:water (24:1, V/V, 25 mL), stirred vigorously on a vortex mixer, and centrifuged. The acetone solution was removed by cannula and the trituration process repeated two more times. The solid was then triturated with diethyl ether using the same process. The pale yellow solid, in the centrifuge tube, was then dried under reduced pressure (0.6 torr, 2 hr). Yield: 0.723 g, 1.63 mmols (82%). MP: decomposition greater than 230° C. $^1$H NMR (D$_2$O, ppm): 6.116 (s, 4H), 7.670 (d, 4H, J=8.25 Hz), 8.017 (d, 4H, J=8.25 Hz), 8.698 (d, 4H, J=6.5 Hz), 9.325 (d, 4H, J=6.5 Hz). $^{11}$B-NMR (CH$_3$OH, ppm): 29 (s).

A stock solution of HPTS-PEG (10 mL, 5×10$^{-5}$ M) was prepared in a 10-mL volumetric flask with pH 7.4 phosphate buffer (0.1 ionic strength). Similarly, a m-BBV solution (25 mL, 0.0025 M) and α-D-Glucose (10 mL, 0.250 M) solution were prepared. Seven different solutions containing HPTS-PEG, m-BBV, and α-D-Glucose were then prepared in pH 7.4 phosphate buffer as described below in Table 3:

TABLE 3

| Volume HPTS-PEG stock (mL) | Volume (Glucose) stock (mL) | Volume m-BBV stock (mL) | Volume Glucose (mL) | Final buffer (M) | Final (HPTS-PEG) (M) | Final (m-BBV) (mg/dL) |
|---|---|---|---|---|---|---|
| 1 | 2 | 0 | 2 | 1.00E−05 | 1.00E−03 | 0.00 |
| 1 | 2 | 0.02 | 1.98 | 1.00E−05 | 1.00E−03 | 18.02 |
| 1 | 2 | 0.04 | 1.96 | 1.00E−05 | 1.00E−03 | 36.03 |

TABLE 3-continued

| Volume HPTS-PEG stock (mL) | Volume (Glucose) stock (mL) | Volume m-BBV stock (mL) | Volume Glucose (mL) | Final buffer (M) | Final (HPTS-PEG) (M) | Final (m-BBV) (mg/dL) |
|---|---|---|---|---|---|---|
| 1 | 2 | 0.2 | 1.8 | 1.00E−05 | 1.00E−03 | 180.16 |
| 1 | 2 | 0.4 | 1.6 | 1.00E−05 | 1.00E−03 | 360.32 |
| 1 | 2 | 1 | 1 | 1.00E−05 | 1.00E−03 | 900.80 |
| 1 | 2 |   | 0 | 1.00E−05 | 1.00E−03 | 1801.60 |

The pH of each sample was independently determined using a pH meter to assure that the pH was constant throughout the series to within ±0.02 pH units.

Each sample was then analyzed on the Perkin-Elmer LS50-B luminescence spectrometer.

The instrumental settings were:

Excitation Wavelength—473 nm

Emission Wavelength Range—480–630 nm

Excitation Slit Width—0 nm (Instrumental dependent minimum)

Emission Slit Width—0 run (Instrumental dependent minimum)

Optical filter—none

Scan Speed—100 nm/sec

The instrumental settings (slit widths, scan speed, optical filters, excitation wavelength, emission wavelength range) were held constant throughout the series analysis. The emission fluorescence intensity was then quantified by integration (the trapezoidal rule approximation method) of the fluorescence intensity curve between 480 and 630 nm. The relative integrated values, were then used to construct a calibration curve: plotting $F/F_0$ vs. glucose concentration (mg/dL), where $F_0$ is the integrated fluorescence intensity of the first sample in Table 3 containing 0 mg/dL glucose.

COMPARATIVE EXAMPLE C

Synthesis and Evaluation of 4,4'-N,N'-bis-(benzyl-2-boronic Acid)-dipyridinium dibromide (a) An oven-dried, 50-mL centrifuge tube is cooled under argon and fit with a magnetic stir bar. 4,4'-Bipyridyl (1.5 mmol, 0.234 g) is weighed out into the tube which is then sealed with a septum and charged with $CH_3OH$ (7 mL). The homogenous solution is stirred at room temperature while mixing. Freshly prepared dimethyl-(2-bromomethyl)-benzeneboronate (4.5 mmols, 1.2 mL, 1.09 g) is added via syringe to the reaction tube and the resulting brown/orange solution is stirred at room temperature (ambient) for 15 hrs. The reaction vessel is then centrifuged (4 mm at 3200 RPM) and the $CH_3OH$ cannulated to a separate flask. The remaining yellow solid is triturated-with diethyl ether (25 mL), stirred vigorously using a vortex mixer, and centrifuged. The ether solution is removed by cannula and the trituration process repeated three more times. The pale yellow solid, in the centrifuge tube, is then dried under reduced pressure (0.6 torr, 2 hr). The yield is 70%. $^1$H-NMR ($D_2O$, ppm): 6.21 (s, 2H), 7.72, (m, 3H), 7.91 (d, 1H), 8.60 (d, 2H), 9.18 (d, 2H). $^{11}$B-NMR ($CH_3OH$, ppm) 30.2 (broad s).

(b) Evaluation of glucose sensitivity with HPTS-PEG. The glucose sensing ability of benzyl viologen was compared to that of 4,4'-N,N'-bis(benzyl-3-boronic acid)-bipyridinium dibromide in the presence of HPTS-PEG dye. The apparent Stem-Volmer quenching constant for benzyl viologen with HPTS-PEG was determined as described in Procedure A, and found to be 559 $M^{-1}$. The glucose sensitivity of benzyl viologen in the presence of HPTS-PEG was determined in the same manner. The signal from the benzyl viologen/HPTS-PEG solution did not respond to changes in glucose concentration. The glucose sensitivity of 4,4'-N,N'-bis (benzyl-3-boronic acid)-bipyridinium dibromide is shown in FIG. 5 together with the glucose sensitivity of benzyl viologen.

(c) Similarly, when A is repeated except that the 4,4'N,N'-Bis (benzyl-3-boronic acid)-bipyridinium dibromide is replaced with 4,4'-N,N'-bis -(benzyl-4-boronic acid) dipyridyl dibromide.

The results for glucose sensitivity are comparable.

EXAMPLE 1

Synthesis of 4-N-(benzyl-4-boronic Acid)-4'-N'-(benzyl-4-ethenyl)-dipyridinium bromide chloride An oven-dried, 50-mL centrifuge tube was cooled under argon, fit with a magnetic stir bar, and charged with 4-(4-pyridyl)-N-(benzyl-4-ethenyl)-pyridinium chloride (0.463 g, 1.5 mmols). The tube was sealed with a septum and charged with acetonitrile (6 mL). The resulting pink/orange suspension was stirred at room temperature while freshly prepared dimethyl-(4-bromomethyl)-benzeneboronate (0.486 g, 2 mmols) was added via syringe. After stirring the suspension for 23 hrs the reaction vessel was centrifuged (4 min at 3200 RPM) and the acetonitrile cannulated to a separate flask. The remaining yellow solid was triturated with acetone:water (25 mL, 24:1, V/V), stirred vigorously on a vortex mixer, and centrifuged. The acetone solution was removed by cannula and the trituration process repeated two more times. The solid was then triturated with diethyl ether using the same process. The bright yellow solid, in the centrifuge tube, was then dried under reduced pressure (0.5 torr, 1 hr). Yield: 0.431 g, 0.824 mmols (55%). MP: >200° C. $^1$H-NMR ($D_2O$, ppm): 5.405 (d, 1H, J=11.5 Hz), 5.929 (d, 2H, J=17.5 Hz), 5.934 (s, 2H), 5.981 (s, 2H), 6.832 (dd, 2H, $J_1$=17.5 Hz, $J_2$=11 Hz), 7.523 (d, 2H, J=9 Hz), 7.562 (d, 2H, J=8 Hz), 7.626 (d, 2H, J=8 Hz), 7.8815 (d, 2H, J=8.5 Hz), 8.566 (dd, 4H, J=3.6 Hz, $J_2$=1.5 Hz), 9.1855 (dd, 4H, $J_1$=6.5 Hz, $J_2$=6 Hz). $^{11}$B-NMR ($CH_3OH$, ppm): 28 (s).

This compound was found to quench the fluorescence of the dye of Example 4 and to respond to glucose.

EXAMPLE 2

Synthesis of 4-N-(benzyl-3-boronic Acid)-4'-N'-(benzyl-4-ethenyl)-dipyridinium bromide chloride An oven-dried, 50-mL centrifuge tube was cooled under argon, fit with a magnetic stir bar, and charged with 4-(4-pyridyl)-N-(benzyl-4-ethenyl)-pyridinium chloride (0.463 g, 1.5 mmols). The tube was sealed with a septum and charged with acetonitrile (6 mL). The resulting pink/orange suspension was stirred at room temperature while freshly prepared dimethyl-(3-bromomethyl)-benzeneboronate (0.486 g, 2 mmols) was added via syringe. After stirring the suspension for 23 hours the reaction vessel was centrifuged (4 min@3200 RPM) and the acetonitrile cannulated to a separate flask. The remaining yellow solid was triturated with acetone:water (25 mL, 24:1, V/V), stirred vigorously on a vortex mixer, and allowed to sit overnight. The acetone solution was removed by cannula and the solid then triturated with diethyl ether (3×25 mL); each time the triturant was removed via cannula. The remaining bright yellow solid, in the centrifuge tube, was then dried under reduced pressure (0.015 torr, 3 hr). Yield: 0.584 g, 1.12 mmols (74%). MP: decomposition>150° C. $^1$H-NMR (D$_2$O, ppm): 5.5165 (d, 1H, J=10.75 Hz), 6.0435 ppm (d, 1H, J=17.8 Hz), 6.095 (s, 2H), 6.049 (s, 2H), 6.9433 (dd, 1H, J$_1$=11.5 Hz, J$_2$=17.9 Hz), 7.626 (m, 4H), 7.724 (m, 2H), 7.979 (s, 1H), 7.994 (d, 1H, J=7.5 Hz), 8.648 (d, 4H), 9.280 (d, 4H). $^{11}$B-NMR (CH$_3$OH, ppm): 28 (s).

This compound was used to make the polymers of Examples 6, 7, 10, and 11.

EXAMPLE 3

Synthesis of N,N',N"-tris-(1-aminoethyl-2-polyethylene glycol-methoxy (n~125))-8-acetoxy-pyrene-1,3,6-tris-sulfonamide A 250-mL round bottom flask was equipped with a magnetic stir bar and charged with 170 mL of dry tetrahydrofuran (THF). Methoxy-polyethyleneglycol (PEG)-amine (5.65 g, 5630 g/mol, 1 mmol) was added to the flask along with 0.5 grams of granular CaH$_2$. The mixture was heated to 30° C. for 24 hr with stirring. Diisopropylethylamine (0.6 mL, 129.24 MW, 0.742 g/mL, 3.4 mmol) was added to the flask and the mixture allowed to stir for an additional hr. The flask was cooled to room temperature and filtered through an air sensitive glass fritted filtration apparatus to remove excess CaH$_2$ and Ca(OH)$_2$. The THF solution was placed back into a 250-mL round bottom flask with magnetic stir bar and heated to 30° C. with stirring. 8-Acetoxy-pyrene-1,3,6-trisulfonyl chloride (0.185 g, 624.8 g/mol, 0.3 mmol) was added to the warm THF solution. The solution immediately turned a deep blue color and faded to a red wine color over 15 min. The reaction was stirred at 30° C. for 24 hr. The solvent was removed by rotary evaporation and the residue was dissolved in 100 mL of 1 M HCl. The aqueous solution was extracted with methylene chloride (3×100 mL). The methylene chloride fractions were combined and the solvent was removed by reduced pressure evaporation to yield compound as a red solid. Yield: about 5.5 g (~97%). FTIR (KBr pellet, cm$^{-1}$): 842, 963, 1060, 1114, 1150, 1242, 1280, 1343, 1360, 1468, 1732, 2525, 2665, 2891. 1.

This product was then used in Examples 4 and 7.

EXAMPLE 4

Synthesis of N,N',N"-tris-(1-aminoethyl-2-polyethylene glycol-methoxy(n~125))-8-hydroxy-pyrene-1,3, 6-tris-sulfonamide Approximately 5.5 g of N,N',N"-tris-(1-aminoethyl-2-polyethylene glycol)-8-acetoxy-1,3,6-tris-sulfonamide was dissolved in 100 mL of 1 M NaOH and stirred for 2 hr. The aqueous solution was neutralized to pH 7 and extracted with methylene chloride (3×100 mL). The methylene chloride fractions were combined and reduced to approximately 10 mL by rotary evaporation. The concentrated methylene chloride solution was then added dropwise into 400 mL of vigorously stirred diethyl ether in an Erlenmeyer flask. The diethyl ether was filtered using a Buchner funnel. The product was isolated as an orange powder. Yield: 5.425 g, 0.31 mmol (94%). FTIR (KBr pellet, cm$^{-1}$): 842, 963, 1060, 1110, 1150, 1242, 1281, 1343, 1360, 1468, 2888. This compound was identified as the trisubstituted sulfonamide derivative by Fourier Transform Infrared (FTIR). The sulfonic acid IR stretch occurs at 1195.7 cm$^{-1}$. There is no 1195.7 cm$^{-1}$ stretch in the FTIR of this compound. Instead a stretch of 1110 cm$^{-1}$, assigned to the sulfonamide, is observed. When dissolved in pH 7.4 buffer the fluorescence of this compound is quenched by methyl viologen with an apparent Stern-Volmer quenching constant of 319M$^{-1}$.

This was quenched by the products of Examples 1 and 2 and used in Example 12.

EXAMPLE 5

Synthesis of N,N',N"-tris-(1-aminopropyl-3-methacrylamide)-8-acetoxy-pyrene-1,3,6-tris-sulfonamide (acetoxy-HPTS-MA)

A 100-mL round bottom flask was charged with aminopropyl-3-methacrylamide HCl salt (2.68 g, 15 mmol) and 50 mL of acetonitrile to give a white suspension. Water was added dropwise while stirring until all of the white suspension had disappeared producing two layers. Potassium carbonate was added and the suspension was stirred for 15 min. The supernatant was transferred to a 500-mL round bottom flask and the potassium carbonate was washed with 50 mL acetonitrile which was then combined in the 500-mL round bottom flask. A yellow solution of acetoxy-HPTS-Cl (1.03 g, 1.8 mmol), 200 mL acetonitrile, and 20 mL dichloromethane was added under argon to the 500 mL round bottom flask containing the free amine in acetonitrile causing the solution to turn dark red with a precipitate formation. The solution was stirred for 1 hr and the supernatant was transferred and concentrated under vacuum to give a dark residue. The residue was extracted with water (1000 mL) and a 50:50 acetonitrite/ethyl acetate solution (700 mL). The organic extract was washed with an additional 1000 mL water. The organic extract was dried over magnesium sulfate and concentrated on a rotary evaporator to give a red residue which was dissolved in methanol. The methanol solution was concentrated and the resulting red residue was dried under high vacuum to give a red solid which was the unprotected HPTS-MA. Yield: 420 mg, 0.5 mmol (28%). $^1$H-NMR (500 MHz, D$_4$-Methanol, ppm): 1.617 (p, J=6.5 Hz, 8H), 1.781 (s, 3H), 1.767 (s, 6H), 2.934 (p, J=6.5 Hz, 9H), 3.158 (mult. 8H), 5.211 (t, J=1.5 Hz), 5.229 (t, J=1.5 Hz), 5.488 (s, 1H), 5.510 (s, 2H), 8.290 (s, 1H), 8.837 (d, J=9.5 Hz, 1H), 8.913 (d, J=9.5 Hz, 1H), 8.988 (d, J=1.5 Hz 1H), 9.201 (d, J=9.5 Hz, 1H), 9.222 (s, 1H). Unprotected HPTS-MA (100 mg, 0.1 mmol) was then suspended in 10 mL acetic anhydride and a catalytic amount of sodium acetate was added and the suspension refluxed for 2 hr. Acetic anhydride and acetic acid were removed under vacuum and the resulting brown residue was extracted with 20 mL acetonitrile. The extract was dripped into 150 mL diethyl ether causing the precipitation of a brown solid. Yield: 75 mg, 0.09 mmol (86%).

This monomer was used in Examples 9, 10 and 11.

EXAMPLE 6

Copolymerization of 4-N-(benzyl-3-boronic Acid)-4'-N'-(benzyl-4-ethenyl)-dipyridinium bromide chloride into a water-soluble polymer A 50-mL cone-shaped round bottom flask was charged with 2-hydroxy ethyl methacrylate (1.50 g, 11.5 mmols), 4-N-(benzyl-3-boronic acid)-4'-N'-(benzyl-4-ethenyl)-dipyridinium bromide chloride (0.1 g, 0.191 mmols), and 3-[(methacryloylamino)propyl] trimethyl ammonium chloride (0.50 g, 2.27 mmols). After the flask was sealed with a septum, the solution was vigorously stirred on a vortex mixer. The vessel was then charged with isopropyl alcohol:water (8 mL, 1:1, V/V) and deoxygenated with argon for one hour. Concurrently, in a separate 100-mL, side-armed round bottom flask, a solution of 2,2'-azobisisobutyronitrile (AIBN, 100 mg, 0.609 mmols) in isopropyl alcohol:water (5 mL) was prepared. The flask was equipped with a magnetic stir bar and a condenser, and deoxygenated with argon for one hour. The entire monomeric solution was taken-up by syringe and 1 mL was added, through the sidearm, to the AIBN solution. The AIBN reaction vessel was then placed in a 70° C. oil bath and the remaining monomeric mixture added via syringe pump over 6 hrs (1.5 mL/hr). The resulting orange solution was cooled to room temperature under argon and the solvent carefully removed in vacuo. The amorphous solid was dissolved in $CH_3OH$ (20 mL) and quantitatively transferred to a centrifuge tube via cannula. After addition of diethyl ether (20 mL) and formation of a white precipitate, the product was isolated via centrifugation (4 min at 3200 RPM). It was washed with diethyl ether (30 mL), dried under reduced pressure (0.5 torr, 3 hrs), and isolated under an inert atmosphere of argon. Yield: 1.345 g, (67 Wt %). The amount of viologen moiety incorporated into the polymer was determined, by UV absorbance, to be greater than 99% of the expected value.

EXAMPLE 7

Semi IPN: The Thin Film Copolymerization of 4-N-(benzyl-3-boronic acid)-4'-N'-(benzyl-4-ethenyl)-dipyridinium bromide chloride using HPTS-PEG A 10-mL volumetric flask was charged with 2-hydroxy ethyl methacrylate (3.525 g, 27.08 mmols), 4-N-(benzyl-3-boronic acid)4'-N'-(benzyl-4-ethenyl)-dipyridinium bromide chloride (0.039 g, 0.075 mmols), 3-[(methacryloylamino)propyl] trimethyl ammonium chloride (0.3 g, 1.36 mmols), polyethylene glycol dimethacrylate (1.11 g, 1.11 mmols), 2,2'-azobis (2-(2-imidazolin-2-yl)propane)dihydrochloride (0.025 g, 0.077 mmols), and N,N',N'-tris-(1-aminoethyl-2-polyethylene glycol (n~125)-methoxy-8-hydroxy-pyrene 1,3,6-tris-sulfonamide) (0.013 g, $7.5 \times 10^{-4}$ mmols); it was filled to the 10-mL mark with isopropyl alcohol:water (1:1, V/V). After the solution was vigorously stirred on the vortex mixer it was transferred, via pipette, to a 50-mL, cone-shaped round bottom flask and deoxygenated with argon for one hour. The monomer solution was taken-up by syringe and the syringe attached to the polymerization chamber. The solution was then inserted into the cell, under argon, to fill the entire cavity of the cell. The chamber was sealed with Teflon plugs and wrapped in two ZIPLOC® freezer bags. The entire unit was submerged in a 40° C. water-bath and heated for 17 hrs. The polymerization chamber was removed from the bath and the bags, and subsequently disassembled to afford a thin green polymeric film. The polymeric film was leached and stored under pH 7.4 phosphate-buffer.

This product was used in Example 8.

* The polymerization chamber was comprised of (1) An IR cell-holder: two stainless steel plates fashioned to contain the cell and the luer ports; (2) A Cell: two glass plates containing a Teflon 0.02" spacer in between, with holes drilled through the top plate and spacer; and (3) A Gasket: a precision-cut rubber spacer used to the seal the cell to the cell-holder.

EXAMPLE 8

Fluorescence Spectroscopy Analysis of Semi IPN: Copolymer of 4-N-(benzyl-3-boronic Acid)-4'-N'-(benzyl-4-ethenyl)-dipyridinium bromide chloride (m-SBBV) using HPTS-PEG A 10-mm path length, 5-mL disposable polystyrene cuvet was modified using a hot metal rod to melt a 3.9 mm diameter hole into the bottom center of the cuvet. While the plastic was still malleable the threads of a 10–32 standard thread, ⅛" I.D. hose end adapter were screwed into the plastic. The plastic was allowed to cool and the adapter was unscrewed. TEFLON® thread tape was applied to the treads. The adapter was then refit into the cuvet. A disposable polyethylene cuvet cap was modified similarly by puncturing a hole in the center of the cap and threading into the hole an identical 10–32 standard thread to ⅛" I.D. hose adapter. A thin sheet of clear plastic was then cut into a 35×9 mm rectangle and a window 6×15 mm was cut out of the center. Two pressure fittings were constructed from the plunger of a Tuberculin Monoject 1-mL syringe. They were used to put pressure on the plastic mask to hold the polymer in place within the cuvet. The round thumb button of the plunger was used as the pressure plate and was removed from the shaft such that the height of the bottom of the plate to the top of the shaft was 9 mm. The flow-through-cell was then assembled such that the polymer film was in the center of the cuvet and the clear plastic mask directly over it, effectively framing the film with its window. The pressure fittings were then put in place using tweezers, one at the bottom of the cell and one at the top, oriented with the broad base against the plastic mask. The out side wall of the cuvet cap, which sits inside the cuvet, was then coated with vacuum grease and inserted into the cuvet to seal the cell. The cell was placed into a Perkin-Elmer LS50B spectrophotometer equipped with a front surface adapter. The cell was oriented so that its side, touching the polymer, was facing the excitation beam of the instrument (face first in the front surface adapter). ⅛" Tygon PTFE tubing was connected to the hose adapters of the flow-through-cell. The orientation of the front surface adapter was optimized so that the emission detector was sensing only the surface of the polymer. A peristaltic pump was used to circulate pH 7.4-phosphate buffer (ionic strength 0.1) through the cell at a rate of 30 mL per minute. The time drive function of the Perkin-Elmer LS50B software was used to acquire fluorescence intensity readings every ten seconds with an integration time of 2 seconds. The excitation frequency was set at 475 nm and the emission frequency was set at 536 nm. The excitation and emission slit widths were set at 2.5 nm. A base line value of 358 (fluorescence intensity) was established with buffer solution. The peristaltic pump was stopped and the pumping solution was changed to 1800 mg/dl glucose in pH 7.4-phosphate buffer. The fluorescence intensity increased 127 units to a value of 485, corresponding to a 35% signal increase (S/N ratio=72). After switching back to buffer the signal approached the expected baseline value of 358.

EXAMPLE 9

N,N',N''-tris-N,N',N'-tris-(1-aminopropyl-3-methacrylamide)-8-hydroxypyrene-1,3,6-tris-sulfonamide hydrogel polymer A 16 mm NMR tube modified with a female 14/20 ground glass joint was charged with a mixture of isopropyl alcohol/water (1:1, 1.5 mL), HEMA (750 mg), polyethylene glycol dimethacrylate (PEGDMA, n~25) (200 mg), 3-(methacryloylamino)-propyltrimethylammonium chloride (TMAC) (50 mg), N,N',N"-tris-(1-aminopropyl-3-methacrylamide)-8-acetoxypyrene-1,3,6-tris-sulfonamide (acetoxy-HPTS-MA) (6) (1 mg, $1.2\times10^{-6}$ mols), and VA-044 free radical initiator (5 mg). All solids were dissolved with the aid of a vortex mixer. The NMR tube was then fitted with a male 14/20 ground glass joint TEFLON® stop cock to vacuum adapter. The mixture was then de-oxygenated via 4 freeze/pump/thaw cycles ($-78°$ C., 1 torr, 5 min. and thawed under nitrogen. The NMR tube was then heated in a water bath at 40° C. ($+0.5°$ C.) for 12 hr. The glass NMR tube was then carefully broken to free the polymer plug. The polymer was dialyzed in 200 mL of de-ionized water with triethylamine (5 drops) (de-ionized water and amine solution was changed each after 24 hr for 7 days) to remove the acetoxy protecting group on the acetoxy-HPTS-MA. The resulting polymer plug was cut into about 5 mm slices and analyzed by fluorescence spectroscopy.

Excitation and emission spectra of the gels are substantially identical to spectra obtained for the PEG adduct (Example 4). Samples of the polymer gel suspended in pH 7.4 buffer are visibly fluorescent when examined in daylight. The fluorescence is noticeably diminished when m-bis benzyl boronic acid viologen is added to the aqueous phase. The fluorescence is recovered when glucose is added to the solution. Similar gels were prepared with dye concentrations of 0.05 to 5 mg/g polymer (dry weight). All were yellow-green to orange in color and were visibly fluorescent when examined in day (natural) light.

Fluoroscence was quenched when hydrogels were exposed to aqueous o-, m-, and p-benzyl boronic acid viologens.

EXAMPLE 10

IPN: Copolymerization of 4-N-(benzyl-3-boronic Acid)-4'-N'-(benzyl-4-ethenyl)-dipyridinium bromide chloride (M-SBBV) using HPTS-MA Monomeric quencher solution: A 10-mL volumetric flask was charged with 2-hydroxy ethyl methacrylate (27.08 mmols, 3.525 g), 4-N-(benzyl-3-boronic acid)-4'-N'-(benzyl-4-ethenyl)-dipyridinium bromide chloride (0.197 mmols, 0.103 g), 3-[(methacryloylamino)propyl] trimethyl ammonium chloride (1.36 mmols, 0.30 g), polyethylene glycol dimethacrylate (1.11 mmols, 1.11 g), and 2,2'-azobis (N,N'-dimethyleneisobutryramidine)dihydrochloride (0.077 mmols, 0.025 g); it was filled to the 10-mL mark with isopropyl alcohol:water (1:1, V/V). The solution was vigorously stirred on the vortex mixer until homogenous.

Polymeric Dye Powder: A 10-mL volumetric flask was charged with 2-hydroxy ethyl methacrylate (27.08 mmols, 3.525 g), 3-[(methacryloylamino)propyl] trimethyl ammonium chloride (1.36 mmols, 0.3 g), polyethylene glycol dimethacrylate (1.11 mmols, 1.11 g), 2,2'-azobis [2-(2-imidazolin-2-yl)propane]dihydrochloride (0.077 mmols, 0.025 g), and N,N',N"-tris-(1-aminopropyl-3'-methacrylamide)-8-acetoxy-pyrene-1,3,6-tris-sulfonamide ($7.5\times10^{-4}$ mmols, $6.6\times10^{-4}$ g); it was filled to the 10-mL mark with isopropyl alcohol:water (1:1, V/V). After the solution was vigorously stirred on the vortex mixer it was transferred, via pipette, to a 50-mL round-bottom flask and the flask was sealed with a rubber septum; it was deoxygenated with argon for 30 minutes. The monomeric solution was taken-up by syringe and the needle was capped with a rubber stopper. It was then transferred to an argon-filled glove box along with the polymerization chamber*. The syringe was attached to the polymerization chamber and the solution was inserted into the cell, under argon, to fill the entire cavity. The chamber was sealed with TEFLON plugs and wrapped in a ZIPLOC® freezer bag. The entire unit was transferred to an oven and heated to 40° C. for 14 hrs. The polymerization chamber was removed from the oven and the bags, and subsequently disassembled to afford a thin green polymeric film. The film was leached with 500 mL of distilled water (pH 5) for six hours; fresh water was replaced every two hours. The thin film was then dried under reduced pressure (40° C., 20 in Hg, 3 hours), brought to $-196°$ C. and crushed into a fine powder using a mortar and pestle.

Interpenetrating network copolymer: A 50-mL round-bottom flask was charged with monomeric quencher-solution (5.2 mL) and polymeric dye-powder (0.169 g). The mixture was vigorously stirred on the vortex mixer for 10 minutes to allow the liquid to be imbibed in the dye particles, and then deoxygenated with argon for 15 minutes. The heterogeneous solution was taken-up by syringe and the needle was capped with a rubber stopper. It was then transferred to an argon-filled glove box along with the polymerization chamber*. The syringe was attached to the polymerization chamber and the solution was inserted into the cell, under argon, to fill the entire cavity. The chamber was sealed with Teflon plugs and wrapped in a Ziploc® freezer bag. The entire unit was transferred to an oven and heated to 40° C. for 14 hrs. The polymerization chamber was removed from the oven and the bag, and subsequently disassembled to afford a thin, orange, gel-integrated polymeric film. The film was placed in a pH 8-NaOH solution for 12 hours, then leached and stored in pH 7.4 phosphate-buffer.

This product was used in Example 13.

\* The polymerization chamber was comprised of (1) An IR cell-holder: two stainless steel plates fashioned to contain the cell and the luer ports; (2) A Cell: two glass plates containing a Teflon 0.02" spacer in between, with holes drilled through the top plate and spacer; and (3) A Gasket: a precision-cut rubber spacer used to the seal the cell to the cell-holder.

EXAMPLE 11

Two Component System: The Thin Film Copolymerization of 4-N-(benzyl-3-boronic acid)-4'-N'-(benzyl-4-ethenyl)-dipyridinium bromide chloride (M-SBBV) using HPTS-MA A 10-mL volumetric flask was charged with 2-hydroxy ethyl methacrylate (3.525 g, 27.08 mmols), 4-N-(benzyl-3-boronic acid)-4'-N'-(benzyl-4-ethenyl)-dipyridinium bromide chloride (0.039 g, 0.075 mmols), 3-((methacryloylamino)propyl) trimethyl ammonium chloride (0.3 g, 1.36 mmols), polyethylene glycol dimethacrylate (1.11 g, 1.11 mmols), 2,2'-azobis (2-(2-imidazolin-2-yl)propane)dihydrochloride (0.025 g, 0.077 mmols) and N,N',N"-tris-(1-aminopropyl-3-methacrylamide)-8-acetoxy-pyrene-1,3,6-tris-sulfonamide ($6.6\times10^{-4}$ g, $7.5\times10^{-4}$ mmols); it was filled to the 10-mL mark with isopropyl alcohol:water (1:1, V/V). After the solution was vigorously stirred on a vortex mixer it was transferred, via pipette, to a 50-mL, cone-shaped round bottom flask and the flask was sealed with a rubber septum; it was deoxygenated with argon for 30 minutes. The monomeric solution was taken-up by syringe and the needle was capped with a rubber stopper. It was then transferred to an argon-filled glove box along with the polymerization chamber*. The syringe was attached to the polymerization chamber and the solution was inserted into the cell, under argon, to fill the entire cavity. The chamber was sealed with TEFLON plugs and wrapped in two ZIPLOC® freezer bags. The entire unit was submerged in a 40° C. water-bath and heated for 12 hrs. The polymerization chamber was removed from the bath and the bags, and subsequently disassembled to afford a thin green polymeric film. The polymeric film was placed in a pH 8-NaOH solution for 12 hours, then leached and stored in pH 7.4 phosphate-buffer.

This product was used in Example 14.

* The polymerization chamber was comprised of (1) An IR cell-holder: two stainless steel plates fashioned to contain the cell and the luer ports; (2) A Cell: two glass plates containing a Teflon 0.02" spacer in between, with holes drilled through the top plate and spacer; and (3) A Gasket: a precision-cut rubber spacer used to the seal the cell to the cell-holder.

EXAMPLE 12

Fluorescence Spectroscopy Analysis of Water Soluble Copolymer of 4-N-(benzyl-3-boronic acid)-4'-N'-(benzyl-4-ethenyl)-dipyridinium bromide chloride (M-SBBV)

A stock solution of water-soluble poly m-SBBV (50 mL, 2.5 mM) was prepared in pH 7.4 phosphate buffer and pH balanced (±0.02 pH units) with NaOH solution. Six different solutions of poly m-SBBV (the analyte, 0, 0.10, 0.15, 0.25, 0.50, 0.75, 1.0 mM) containing HPTS-PEG (dye, $1 \times 10^{-5}$ M) were then prepared and analyzed on the spectrofluorimeter. The analyte/dye solutions were contained in a standard 10-mm path length, quartz cuvet, and the spectrofluorimeter was set to an excitation and emission frequency of 473 and 533, respectively. The excitation and emission slit widths were set to 0 nm. The apparent Stem-Volmer quenching constant was 733 $M^{-1}$. After the fluorescence spectra were obtained for the solutions mentioned above, additional spectra of the analyte/dye solutions were obtained in the presence and absence of glucose and fructose. The apparent differences in spectra were quantified as areas under the curve. The difference in areas was then determined to be representative of the poymer's response to glucose or fructose. In the absence of glucose or fructose the representative area under the curve was determined to be 26479.45. Upon addition of different concentrations of glucose, the areas changed accordingly as indicated in Table 4 below.

TABLE 4

CHANGE IN FLUORESCENCE INTENSITY OF 1.0 MM POLY M-SBBV/HPTS-PEG SOLUTIONS AFTER ADDITION OF GLUCOSE; REPRESENTED AS THE AREA UNDER THE CURVE

| (Glucose) (mg/dl) | Area Under Curve |
|---|---|
| 0 | 26479.45 |
| 18 | 26934.93 |
| 36 | 27163.92 |
| 180 | 27988.86 |
| 360 | 28221.08 |
| 900 | 28810.57 |
| 1800 | 29434.23 |

Thus, the fluorescence intensity increased by 11% upon addition of 1800 mg/dl of glucose and 14.6% upon addition of 1800 mg/dl of fructose.

EXAMPLE 13

Fluorescence Spectroscopy Analysis of IPN: Copolymer of 4-N-(benzyl-3-boronic acid)-4'-N'-(benzyl-4-ethenyl)-dipyridinium bromide chloride (M-SBBV) using Dispersed HPTS-MA Hydrogel A 10-mm path length, 5-mL disposable polystyrene cuvet was modified using a hot metal rod to melt a 3.9 mm diameter hole into the bottom center of the cuvet. While the plastic was still malleable the threads of a 10–32 standard thread, 1/8" I.D. hose end adapter were screwed into the plastic. The plastic was allowed to cool and the adapter was unscrewed. Teflon® thread tape was applied to the treads. The adapter was then refit into the cuvet. A disposable polyethylene cuvet cap was modified similarly by puncturing a hole in the center of the cap and threading into the hole an identical 10–32 standard thread to 1/8" I.D. hose adapter. A thin sheet of clear plastic was then cut into a 35×9 mm rectangle and a window 6×15 mm was cut out of the center. Two pressure fittings were constructed from the plunger of a Tuberculin Monoject 1-mL syringe. They were used to put pressure on the plastic mask to hold the polymer in place within the cuvet. The round thumb button of the plunger was used as the pressure plate and was removed from the shaft such that the height of the bottom of the plate to the top of the shaft was 9 mm. The flow-through-cell was then assembled such that the polymer film was in the center of the cuvet and the clear plastic mask directly over it, effectively framing the film with its window. The pressure fittings were then put in place using tweezers, one at the bottom of the cell and one at the top, oriented with the broad base against the plastic mask. The out side wall of the cuvet cap, which sits inside the cuvet, was then coated with vacuum grease and inserted into the cuvet to seal the cell. The cell was placed into a Perkin-Elmer LS50B spectrophotometer equipped with a front surface adapter. The cell was oriented so that its side, touching the polymer, was facing the excitation beam of the instrument (face first in the front surface adapter). 1/8" Tygon PTFE tubing was connected to the hose adapters of the flow-through-cell. The orientation of the front surface adapter was optimized so that the emission detector was sensing only the surface of the polymer. A peristaltic pump was used to circulate pH 7.4-phosphate buffer (ionic strength 0.1) through the cell at a rate of 30 mL per minute. The time drive function of the Perkin-Elmer LS50B software was used to acquire fluorescence intensity readings every ten seconds with an integration time of 2 seconds. The excitation frequency was set at 475 nm and the emission frequency was set at 536 nm. The excitation and emission slit widths were set at 15 nm and 20 nm, respectively. A base line value of 249 (fluorescence intensity) was established with buffer solution. The peristaltic pump was stopped and the pumping solution was changed to 1800 mg/dl glucose in pH 7.4-phosphate buffer. The fluorescence intensity increased 25 units to a value of 274, corresponding to a 10% signal increase (S/N ratio=43). After switching back to buffer the signal approached the expected baseline value of 249.

EXAMPLE 14

Fluorescence Spectroscopy Analysis of Two Component System: Thin Film Copolymer Hydrogel of 4-N-(benzyl-3-boronic acid)-4'-N'-(benzyl-4-ethenyl)-dipyridinium bromide chloride (M-SBBV) using HPTS-MA A 10-mm path length, 5-mL disposable polystyrene cuvet was modified using a hot metal rod to melt a 3.9 mm diameter hole into the bottom center of the cuvet. While the plastic was still malleable the threads of a 10–32 standard thread, 1/8" I.D. hose end adapter were screwed into the plastic. The plastic was allowed to cool and the adapter was unscrewed. Teflon® thread tape was applied to the treads. The adapter was then refit into the cuvet. A disposable polyethylene cuvet cap was modified similarly by puncturing a hole in the center of the cap and threading into the hole an identical 10–32 standard thread to 1/8" I.D. hose adapter. A thin sheet of clear plastic was then cut into a 35×9 mm rectangle and a window 6×15 mm was cut out of the center.

Two pressure fittings were constructed from the plunger of a Tuberculin Monoject 1-mL syringe. They were used to put pressure on the plastic mask to hold the polymer in place within the cuvet. The round thumb button of the plunger was used as the pressure plate and was removed from the shaft such that the height of the bottom of the plate to the top of the shaft was 9 mm. The flow-through-cell was then assembled such that the polymer film was in the center of the cuvet and the clear plastic mask directly over it, effectively framing the film with its window. The pressure fittings were then put in place using tweezers, one at the bottom of the cell and one at the top, oriented with the broad base against the plastic mask. The out side wall of the cuvet cap, which sits inside the cuvet, was then coated with vacuum grease and inserted into the cuvet to seal the cell. The cell was placed into a Perkin-Elmer LS50B spectrophotometer equipped with a front surface adapter. The cell was oriented so that its side, touching the polymer, was facing the excitation beam of the instrument (face first in the front surface adapter). ⅛" Tygon PTFE tubing was connected to the hose adapters of the flow-through-cell. The orientation of the front surface adapter was optimized so that the emission detector was sensing only the surface of the polymer. A peristaltic pump was used to circulate pH 7.4-phosphate buffer (ionic strength 0.1) through the cell at a rate of 30 mL per minute. The time drive function of the Perkin-Elmer LS50B software was used to acquire fluorescence intensity readings every ten seconds with an integration time of 2 seconds. The excitation frequency was set at 475 nm and the emission frequency was set at 536 nm. The excitation and emission slit widths were set at 7 nm. A base line value of 490 (fluorescence intensity) was established with buffer solution. The peristaltic pump was stopped and the pumping solution was changed to 400 mg/dl glucose in pH 7.4-phosphate buffer. The fluorescence intensity increased nine units to a value of 499, corresponding to a 1.5% signal increase (S/N ratio= 6.5). The process of switching solutions was repeated. The buffer gave an expected base line of 490. After changing to 1800 mg/dl glucose in pH 7.4-phosphate buffer the fluorescence intensity rose 35 units to a value of 525, corresponding to a 7.6% signal increase (S/N=15.0). Finally, the base line dropped to the expected value of 490 when buffer was pumped through the system.

While only a few embodiments of the invention have been shown and described herein, it will become apparent to those skilled in the art that various modifications and changes can be made in a glucose sensor and its components including the fluorophore dye, quencher and optional polymer matrix for monitoring polyhydroxyl-containing organic analytes, primarily for in vivo glucose monitoring, without departing from the spirit and scope of the present invention. All such modifications and changes coming within the scope of the appended claims are intended to be carried out thereby.

We claim:

1. An optical method for the in vivo detection of polyhydroxyl-substituted organic molecules as the analyte between about 430 and 800 nm detection in physiological media having a p11 of about 7.3–7.5, which method comprises:
    A. obtaining a flurorophore dye D, which is compatible with the analyte solution, wherein D is selected from:
        (a) $D^1$ which is a fluorophore dye having the properties of:
            i. A fluorophore,
            ii. An excitation in the range greater than 430 nm and less than 800 nm,
            iii. Resistant to photobleaching under the conditions of analysis,
            iv. A Stokes shift of about or greater than 30 nm,
            v. Compatibility with said analyte solution, and wherein said
            vi. Dye $D^1$ is quenched by methyl viologen to produce an experimentally determined Stern-Volmer quenching constant (Ksv) greater than or equal to 50,
            wherein the fluorophore dye $D^1$ is selected from the group consisting of
                (i) a discrete compound having a molecular weight of 1,000 daltons or greater and
                (ii) a pendant group or chain unit which is also attached to a water soluble or dispersible polymer which has a molecular weight greater than about 10,000 daltons, wherein optionally said water soluble or dispersible polymer is non-covalently associated with water insoluble polymer matrix $M^1$ and is thus physically immobilized within said polymer matrix $M^1$, and wherein said polymer matrix $M^1$ is permeable to or in contact with said analyte solution;
        (b) $D^2$ is a fluorophore dye having the properties of:
            i. A fluorophore,
            ii. An excitation in the range greater than 430 nm and less than 800 nm,
            iii. A Stokes shift of about or greater than 30 nm,
            iv. Resistant to photobleaching under the conditions of analyses,
            v. Compatibility in the analyte solution, and wherein
            vi. Said Dye $D^2$ is quenched by methyl viologen to produce an Stern-Volmer quenching constant (Ksv) greater than or equal to 50, wherein $D^2$ is covalently bonded to an insoluble polymer matrix wherein said polymer matrix $M^1$ is permeable to or in contact with said analyte; wherein said fluorophore dye $D^2$ is a part of the structure:

$$M^1\text{—}L^1\text{—}D^2$$

wherein:
   $M^1$ is said polymer matrix,
   $L^1$ is a hydrolytically stable covalent linking group selected from the group consisting of a direct bond, a lower alkylene having 1 to 8 carbon atoms which alkylene is optionally terminated with or includes one or more divalent groups selected from the group consisting of sulfonamide, amide, ester, ether, sulfide, sulfone, phenylene, urethane, urea, and amine; and $D^2$ is said fluorophore dye which is covalently bonded to said polymer matrix $M^1$; with the proviso that $D^2$ which is polyfunctional is bonded to matrix $M^1$ at one, two or three sites;

B. combining the components of step A with a analyte solution-compatible quencher molecule Q having at least one boronic acid functional group, wherein Q is a conjugated nitrogen-containing heterocyclic, aromatic bis-onium salt selected from:
    (i) $Q^1$ which is a pendant group or a chain unit in a water-soluble or water-dispersable polymer having a molecular weight greater than 10,000 daltons and said polymer optionally is non-covalently associated with the optional polymer matrix $M^1$ when present and immobilized within said polymer matrix wherein $Q^1$ is a compound having the properties of:
        compatibility in said analyte solution,
        produces a detectable change in the emission of the dye in the presence of said analyte, or
    (ii) $Q^2$ which is a structure having the properties of:
        compatibility in said analyte solution
        produces a detectable change in the emission of the dye in the presence of said analyte, wherein $Q^2$ is covalently bonded by linking group $L^2$ to $M^1$ or to a second water insoluble polymer matrix $M^2$ producing $M^2$—$L^2$—$Q^2$ wherein $L^2$ is selected from the group consisting of a direct bond and a lower alkylene having 1 to 8 carbon atoms which alkylene is optionally terminated with or includes one or more divalent groups selected from the group consisting of sulfonamide, amide, ester, ether, sulfide, sulfone, phenylene, urea, thiourea, urethane, and amine, wherein said quencher $Q^1$ or $Q^2$ is mixed at a molecular level with said fluorophore dye $D^1$ or $D^2$, and with the proviso that $Q^2$ being polyfunctional is linked to the matrix $M^2$ at one or two sites, thus creating a device including the components of step A and step B C. contacting the in vivo physiological fluid with said device which contains analyte, a dye and a quencher in vivo with an excitation light source coupled with a detector;

D. producing a detectable and quantifiable signal in the range of about 430 to 800 nm; and E. determining the concentration of said polyhydroxyl-substituted analyte in said physiological fluid.

2. The method of claim 1 wherein the Dye $D^1$ is selected from the group consisting of pyranine derivatives having the structure of:

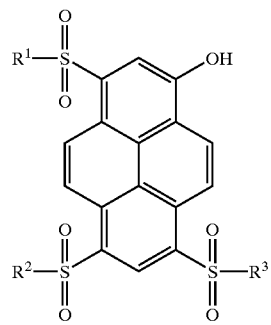

where $R^1$, $R^2$ and $R^3$ are each —$NHR^4$
wherein $R^4$ is —$CH_2$—$CH_2$(—O—$CH_2$—$CH_2$)$_n$—$X^1$;
wherein $X^1$ is selected from —OH, —$OCH_3$, —$CO_2H$, —$CONH_2$, —$SO_3H$, or —$NH_2$; and n is between about 100 and 10,000.

3. The method of claim 1 wherein the Dye $D^1$ is selected from the group consisting of pyranine derivatives having the structure of:

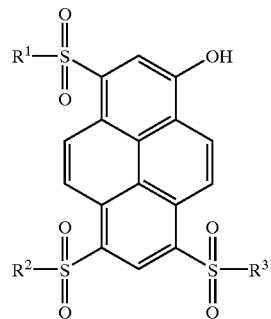

where $R^1$, $R^2$ and $R^3$ are each —NH—$CH_2$—$CH_2$(—O—$CH_2$—$CH_2$)$_n$—$X^1$, and $X^1$ selected from —OH, —$OCH_3$, —$CO_2H$, —$CONH_2$, —$SO_3H$, or —$NH_2$, n is about 70 to 10,000.

4. The method of claim 1 wherein the Dye $D^2$ is prepared from pyranine derivatives and comprises a group which is a reaction product of a compound of the structure:

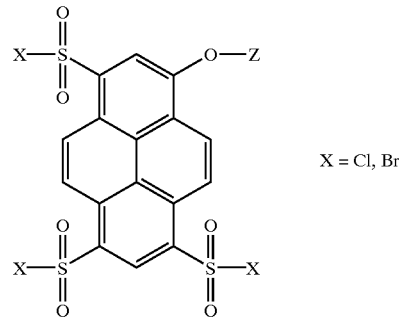

X = Cl, Br or a dye monomer

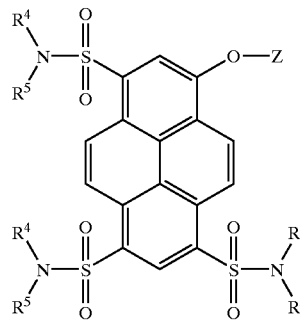

where $R^4$=—H and
$R^5$ is selected from —$R^6$—NH—(C=O)—(C=$CH_2$)—$R^7$, —$R^6$—O—(C=O)—(C=$CH_2$)—$R^7$,
or —$CH_2$—$C_6H_4$—CH=$CH_2$ or —$CH_2$ CH=$CH_2$, and where $R^6$ is lower alkylene having 2 to 6 carbon atoms and
where $R^7$ is —H, or; —$CH_3$ and
Z is a blocking group that can be removed by hydrolysis) selected from:

—(C=O)—$R^8$—Y where $R^8$ is a lower alkylene having 1 to 4 carbon atoms and Y is selected from —H, —OH, —$CO_2H$, —$SO_3H$, —(C=O)—NH—$R^9$ or —$CO_2$—$R^9$,
where $R^9$ is a lower alkyl having 1 to 4 carbon atoms.

5. The method of claim 1 wherein the quencher $Q^2$ comprises a group which is a reaction product of a compound of a structure selected from the group consisting of

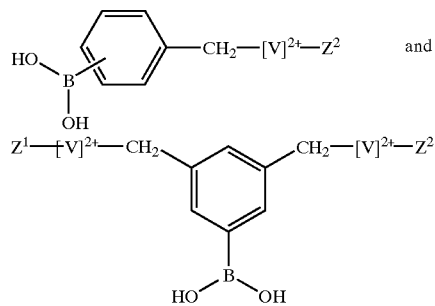

where $(V)^{2+}$ is a nitrogen containing conjugated heterocyclic aromatic group selected from isomers of dipyridyls dipyridyl ethylenes, dipyridyl phenylenes, phenanthrolines, or diazafluorenes; and where $Z^1$ or $Z^2$ is either a polymerizable ethylenically unsaturated group selected from:

(i) $-R^{10}-CO_2-C(R^{11})=CH_2$, $-R^{10}-NH-(C=O)-C(R^2)=CH_2$, or $-CH_2-C_6H_4-CH=CH_2$, here $R^{10}$ is a lower alkylene or hydroxyalkylene of 2 to 6 carbon atoms and where $R^{11}=-H$ or $-CH_3$; or (ii) a coupling group selected from: $-R^{12}-Y^1$ where $R^{12}$ is $-CH_2C_6H_4-$ or alkylene of 2 to 6 carbon atoms and $Y^1$ is $-OH$, $-SH$, $-CO_2H$, or $-NH_2$.

6. The method of claim 5 where the quenchers comprise a reaction product of a compound of the structure:

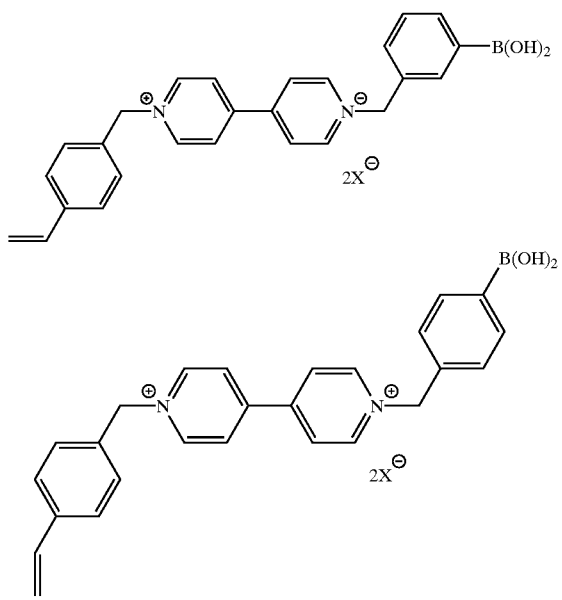

wherein X is chloride or bromide.

7. The method of claim 1 wherein in substep A, the fluorophore is $D^1$.

8. The method of claim 1 wherein in substep A, the fluorophore $D^2$ comprises a group which is a reaction product of a compound of the structure:

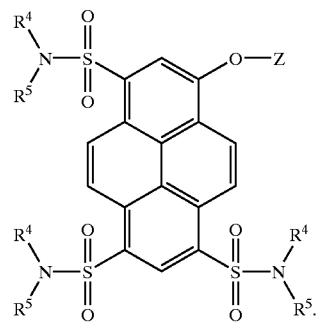

9. The method of claim wherein in substep B, quencher Q is $Q^1$.

10. The method of claim 1 wherein in substep B, quencher $Q^2$ comprises a group which is a reaction product of a compound of the structure:

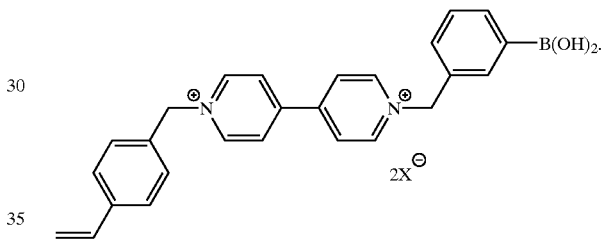

11. The method of claim 1 wherein in substep A, D is $D^1$ and in substep B, Q is $Q^1$.

12. The method of claim 1 wherein in substep A the fluorophore $D^1$ is selected from pyranine derivatives having the structure of:

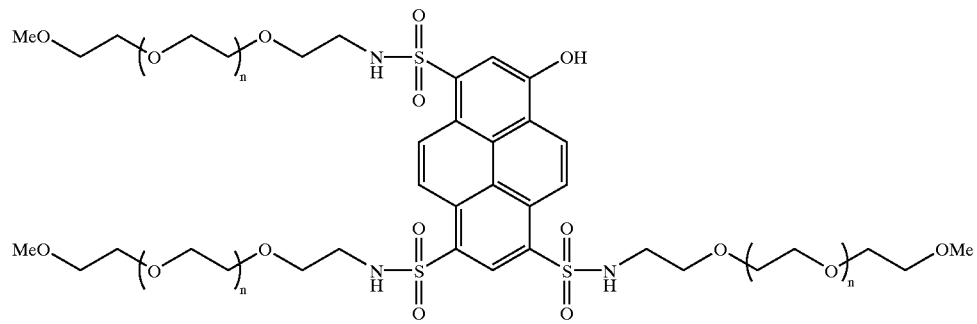

wherein n is between about 70 and 200.

13. The method of claim 1 wherein in substep A the polymeric dye $D^2$ comprises a group which is a reaction product of a compound of the structure:

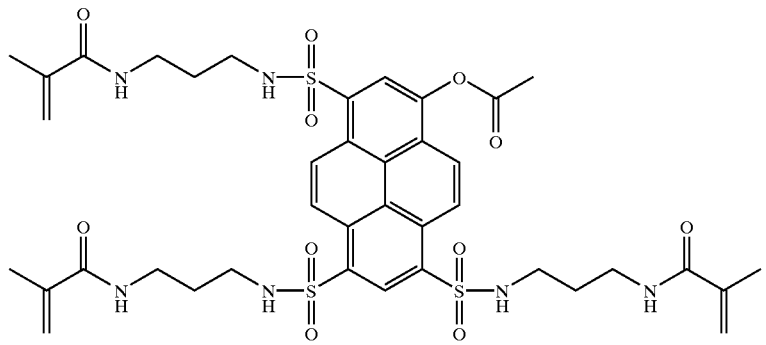

and in step B the quencher comprises a group which is a reaction product of a monomer selected from the group consisting of

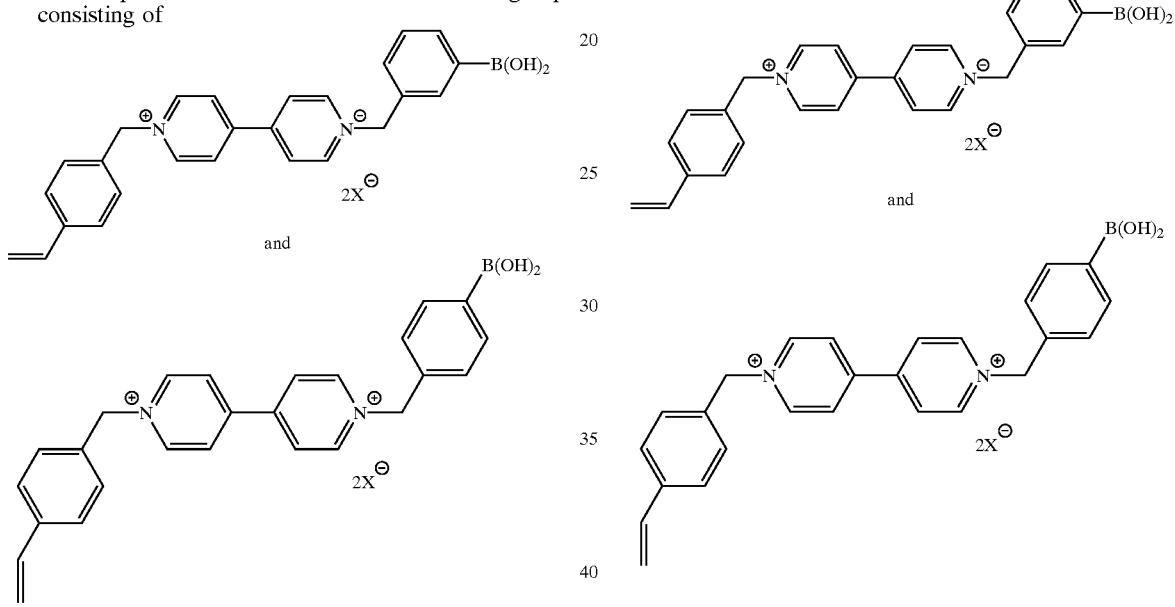

wherein X is bromide or chloride.

14. The method of claim 1 wherein the polyhydroxyl-substituted organic molecules which are detected are sugars selected from the group consisting of glucose and fructose.

15. The method of claim 14 wherein the Dye $D^1$ is selected from the group consisting of

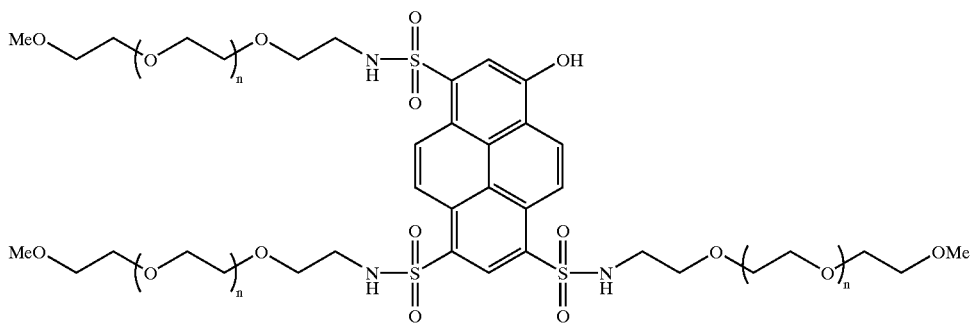

wherein n is about 70 to 200.

16. The method of claim 14 wherein the quencher $Q^2$ comprises a structure which is a reaction product of a monomer selected from the group consisting of wherein X is bromide or chloride.

17. An in vivo optical sensing device wherein the Dye D components and quencher Q components are immobilized within or covalently attached to a polymer matrix $M^1$, $M^2$ or combinations thereof as defined in claim 1 and said device measures the concentration of polyhydroxyl-containing molecules within an in vivo biological medium periodically or continuously.

* * * * *